(12) United States Patent
Fujisawa et al.

(10) Patent No.: US 6,259,003 B1
(45) Date of Patent: Jul. 10, 2001

(54) COTTON PLANT PROMOTERS

(75) Inventors: Koichi Fujisawa; Yoshihisa Kasukabe; Susumu Nishiguchi; Yoshihiko Maekawa, all of Otsu (JP); Randy Dale Allen; Song Ping, both of Lubbock, TX (US)

(73) Assignees: Toyo Boseki Kabushiki Kaisha, Osaka (JP); Texas Tech University of Lubbock, Lubbock, TX (US)

( * ) Notice: Subject to any disclaimer, the term of this patent is extended or adjusted under 35 U.S.C. 154(b) by 0 days.

(21) Appl. No.: 09/009,443

(22) Filed: Jan. 20, 1998

(30) Foreign Application Priority Data

| Jan. 21, 1997 | (JP) | ..................................... 9-008816 |
| Feb. 3, 1997 | (JP) | ..................................... 9-020638 |
| Feb. 3, 1997 | (JP) | ..................................... 9-020639 |

(51) Int. Cl.$^7$ ............... A01H 5/00; A01H 5/10; C07H 21/04; C12N 5/14; C12N 15/82
(52) U.S. Cl. ............... 800/314; 435/320.1; 435/419; 536/24.1; 800/287
(58) Field of Search .................. 536/24.1; 435/320.1, 435/419, 468; 800/278, 287, 298, 314

(56) References Cited

U.S. PATENT DOCUMENTS 5,620,882 * 4/1997 John ............................. 435/172.3

FOREIGN PATENT DOCUMENTS 0 754 757   1/1997 (EP).
WO 94/12014  6/1994 (WO).

OTHER PUBLICATIONS

Rinehart JA, et al. "Tissue–specific and developmental regulation of cotton gene FbL2A." Plant Physiol. 112: 1331–1341, 1996.*

Benfey PN, et al. "The cauliflower mosaic virus 35S promoter: Combinatorial regulation of transcription in plants." Science 250: 959–966, Nov. 1990.*

Kim Y, et al. "A 20 nucleotide upstream element is essential for the nopaline synthase (nos) promoter activity." Plant Mol. Biol. 24: 105–117, 1994.*

Rinehart et al., "Tissue–Specific and Developmental Regulation of Cotton Gene FbL2A", *Plant Physiol.* 112:1331–1342 (1996).

Hohn et al., "Cauliflower Mosiac Virus: A Potential Vector for Plant Genetic Engineering", *Molecular Biology by Plant Tumors*, Chapter 22, pp. 548–561 (Academic Pres, 1982).

Hoekema et al., "A binary plant vector strategy based on separation of *vir*–and T–region of the *Agrobacterium tumefaciens* Ti–plasmid", *Nature* 303:179–180 (1983).

Bayley et al., "Engineering 2,4–D resistance into cotton", *Theor. Appl. Genet.* 83:645–649 (1992).

Maliyakal John et al., "Gene expression in cotton (*Gossypium hirsutum* L.) fiber: Cloning of the mRNAs", *Proc. Natl. Acad. Sci.* USA 89:5769–5773 (1992).

* cited by examiner

Primary Examiner—Amy J. Nelson
(74) Attorney, Agent, or Firm—Morrison & Foerster LLP

(57) ABSTRACT

Novel plant promoters isolated from cotton fiber tissues are provided. The plant promoters are located upstream cotton plant genes KC03, KC18, KC22, and Gh3, all of which are expressed in cotton fibers, and contain (a) DNA having the nucleotide sequence of SEQ ID NO:1, 6, 11, or 16. Also provided are plant expression vectors prepared by introducing the plant promoters into appropriate vectors; transformed plant cells prepared by introducing the plant expression vectors into host plant cells; transformed plants regenerated from the transformed plant cells; transformed plant seeds obtained from the transformed plants; and processes for producing transformed plants from the plant seeds.

30 Claims, 25 Drawing Sheets

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 1676 base pairs
      (B) TYPE: nucleic acid
      (C) STRANDEDNESS: double
      (D) TOPOLOGY: linear (ii) MOLECULE TYPE: Genomic DNA (iii) ORIGINAL SOURCE:
      (A) ORGANISM: Gossypium barbadense
      (F) TISSUE TYPE: seedling (iv) IMMEDIATE SOURCE:
      (B) CLONE: GKC03

(vi) SEQUENCE DESCRIPTION: SEQ ID NO: 1:

```
GAATTCGACA AGCAACCGTA AAAGATTGAT TAATCGGACG AAAGATTATT GTTAAATTGC      60

AATAATCCAT AAATATGAAA TCCTATTATT GATACGAAGG CACTTACCAA TTCTTTAACA     120

ATGTTAACGG ATGCTATGGA TGGTAATCTC TAAAAGTCCA TAAAAATATT ATTTTATATA     180
```

```
AAATCTATAT TTCAAAATTT AAGAAAAATA AATTAAATAT CATGCATATT ATATAAAAGT      240

AAAACCTAAG TCCTATGCCA CAGTTTAGGT TAAGTGGTAC AGTTCCTAAA ATAATAGAAA      300

TTTTTAATAA TAAATCCAAA TTTTTTTTAC CAATTTAGTC GTTATTTTAA ATATTAAAAA      360

AAGTATGAAA TTGAAAAAAT TAGCAAATGA AATTGAAAAA AATTAGCTTT TTTATTAAAT      420

AAAACAAATT TATAAAACTA AAAAAATAAA GTTTATTTAA AAATGTATAA AATACAAAAA      480

CAAAGTACAT GTGAAAAAGG TATCGCTACT TGTTTGGCGG CACTCCTTTT GAAATTAAAA      540

TACTGGATAC CACTCCTTTT GAAATTAAGA TATTATTATT TAATTGTTAT TTTATTTATT      600

TTTATTAAAA TATTATTTTT TAGAGGTGGT GTCGACTAAT ACATTGACAA CACAGCATTT      660

TACTATTTAA AATAATCTAT TATCATGAAT AGTTTGCTTT TTGCCCCATT TTCATAATTA      720

ATTGTTTCCA TATTATTAAT GTAAAAAACC CTAAATTGAT CTCTCACAAA AATCAAAATA      780

ATCAATCATG ATAAATAATG TGTTTCATTA ATTGTACATA ATTTTTTATT AATATAATAA      840

TAAATTAAGC TTTCAATATT TACAGATTCT ATCAAATTGA TCCTAATTCT AAATATATAA      900

TTATCTTATA TATATATATA AAAGAAGATG TTTAAACTTT GAAAATTAAC TTCAGTTTTT      960

TGAATGATGG AAAAACTTTA ATGGATGTCA TTAATTGTCT CTAAGTACTC ATTTTTTAAA     1020

TTGGTAGAGA TTAAATTGCT TCAGTTTTTT TAGAGGAATT AATGTACTTA ATATAAAAAT     1080

TTTAAAAAAA TTTAACATCT TCTTTATTCG TATATTTATA AGTGTCTATA TCCATTTTAC     1140

GACAGATAAA CCTAATTATA TCCTAACTAA ATAATATTCG GATAAAACTT TTTAAAAATT     1200

TTAACTCCAC ATTTTAAATT TAATCTGACA AATAAATGAA CTTCCACTTC ATTCAAGTTA     1260

GTAAATACAT GGATATCATA TTATATAATC TTAAACATAA TCAGGCAAGC TTATGACCCG     1320

AAGTCTCGAA TGGTCGGATT TTGTGTGTCG GTTAATTAAA TATGGATATG AAATGGCTGT     1380

GTTTTATTTG GATAAAGCAC CACTTTAGCA GACACAGTCC TTGGGCTAAC TTTTAAATTA     1440

ACAAGGGTGG TTGGATTGAA TTGAATAAAA TAAAAATCTT TAATGTTTTT TAAATAAAAT     1500

TTGAATTTTA ACTCAATTTA ATTACCAAAT ACCTTCTTTA AGTAAGGCGT CAGTGATCTG     1560

GTGAAGCTGG CAAGTAGCAT TTATTGGACC AAGTAAATAG CAGCTGCAAT CTCTATTTAA     1620

ACCACAACCC AGTGTCTGAC CAATGCACCA AAGGGTAGTG TGAGCTCTTA CCAATG        1676
```

(2) INFORMATION FOR SEQ ID NO: 2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 2:

```
CCTTCACTGG AACAGGAGCA GC                                                22
```

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 3:

```
CAACAAGCAC AAATGTCC                                                     18
```

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 4:

```
TGTTGAAACA AGCAGAAAAG TGGC                                    24
```

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 5:

```
TCCTTGAAAA GCCCAACCAA AGCC                                    24
```

(2) INFORMATION FOR SEQ ID NO: 6:

(i) SEQUENCE CHARACTERISTICS:
        (A) LENGTH: 1683 base pairs
        (B) TYPE: nucleic acid
        (C) STRANDEDNESS: double
        (D) TOPOLOGY: linear (ii) MOLECULE TYPE: Genomic DNA (iii) ORIGINAL SOURCE:
        (A) ORGANISM: Gossypium barbadense
        (F) TISSUE TYPE: seedling (iv) IMMEDIATE SOURCE:
        (B) CLONE: GKC18

(vi) SEQUENCE DESCRIPTION: SEQ ID NO: 6:

```
AAGCTTCAAA TCTTGAGGTT TTGATGGAAG TTTTGTCCTG TGAATTTTTC TATAATATGT      60

TATTTGGTAT TCAAGTTTTA ATTTTTTTTA ATGTAGTAAT TGTGTTTTTT TTTGTCTAAT     120

ATGATACTTG TATTTGAAAG AAGTTATATA TTATGGTACT TAAAGATAAT TGTGCTAATT     180

TTTTAGTGTT TAATTCGAAT TTTAAGGTTG ATTTGATGGA AGTCAATTGC TAATATTATT     240

AGGTTTGAAT TTTTCATAAT TTTGTTAATA AAATAAATTT AGTTTTAATT GCTAATATTA     300

TCAGCTAATT ATGAATTTTT GTCAAACAAT TCTAAAACCT GAATCAAACA CTAAAAAGTT     360

AACATTTTTA CCTATAAGTG TCAAAATTTA TAATTTTGTC AAATATATAT ACCATATTGG     420

ACCAAAAAAT AACACAAATG CCACATTAAA AAAGTGTTAA ATTTAGATAT CAAATATGTA     480

TTAGTATTTT TTACTTTTCA TTTTTATGGA AAAAATAGCT CTCACCACTT ATCAAGAGAA     540

CCACTTTGCA TTCAACTTAA CAATGCGGTC ATAAGATAAA TGTATCCAAT TACCTTTCGA     600

ATCAGGACTA TGAGTGGCTT TATGTTGTCC AAAAGAATCA TGCTTAAGCG CTCCAAAATA     660

TTGTTTTGCC TAGTTTATTG AAAATCTAAT AATCTCAACG GAGTTCCAAG TAAATTAAAA     720

AGATTAGACC AAAAAACCCC ACATTGAATA ACACAAATAT AGAAATAGTA TGGACTGAAA     780

AAGAAAAAGA AATATGCACA AGTTAATGTT TAAAATAAAG GAATAAATTT ATTCTATGAT     840
```

-continued

```
TAAGAAATGA AATTAAATAT CACATGATTT TTTTTTTTGT TTAGAAAAAG AGAGAAGGAT      900

TCTGGAACTT CATTAACCAA GGATGTAAAA GCCGTTTAAT ACAAAAATAA ATGTCATCAT      960

CATCGAAACT ACATCCGAGT ATCCGACTAA CTACCCTAGA TTAGTATAAG ATTTATTATC     1020

GAATAACATT CTCTCTCTCT TTTTTTTTGA ACGAACATTC TTTTTTTTTC TATTACCATA     1080

GTTTAAGGAA ATTACGATTT TTTTACTATA TTTCCTTAAT TAATTATTTA ATTATTTATT     1140

AATTTAGGAA ATGTAACATT TTGTCTGTTG CATTGTTTTT TGTTCTTTTA TTTTCATAAT     1200

CACAAAAAAT TTACTAGATT ATAATCAGCT AAACCAAACA ACTTTTTAAT ACAAAATTAA     1260

GCATGGATAA ATAAATTAAA AATTATAATT TTTTTAATAA AGGTATTCCA AACAAACTAT     1320

AAGCTAAGAA AAGAAAAAAG TTGGAGGAAA AATGGTGTGA AATTTTGTTT CCTTTACAAG     1380

TTAGAGCTGA AACAACCCAT CTTCCTAATT GATTAGAGTA AGTGAGAGAG AGGTAAAAAA     1440

CTCATTATAG TGGCTCTAAC CTCCAACCAA ATATTAATAA AAAGACAAAT GCATAACGAC     1500

TCATGGATCC ATAGGTTTAT AAAAGATGAT ATGGATGGGT CGTTGAGAGT CATTACTTAT     1560

TACTGCTCTA CACCGACTGA CATTGAATAC CATAGAAGCG CCCCCAATCA CTATAAATAT     1620

TAATGCACCC CTTTCCCCTT ATTTCTCAAT CCCCCTCCTC TTTTGTTGTG AAGAAAAAAA     1680

TGG                                                                  1683

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 7:

CCAACCTAAA CAGCCCAACC                                                   20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 8:

CTTTGGTTCA GCCTCCACCG                                                   20

(2) INFORMATION FOR SEQ ID NO: 9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 9:

ACCATGGTTT TCTTCACAAC AAAAGAGG                                          28

(2) INFORMATION FOR SEQ ID NO: 10:

(i) SEQUENCE CHARACTERISTICS:
```

(A) LENGTH: 20 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 10:

CCGAAGGGAT TGATGGAACC                                                   20

(2) INFORMATION FOR SEQ ID NO: 11:

(i) SEQUENCE CHARACTERISTICS:
        (A) LENGTH: 1603 base pairs
        (B) TYPE: nucleic acid
        (C) STRANDEDNESS: double
        (D) TOPOLOGY: linear (ii) MOLECULE TYPE: Genomic DNA (iii) ORIGINAL SOURCE:
        (A) ORGANISM: Gossypium barbadense
        (F) TISSUE TYPE: seedling (iv) IMMEDIATE SOURCE:
        (B) CLONE: GKC22

(vi) SEQUENCE DESCRIPTION: SEQ ID NO: 11:

AAGCTTTTTA GGTAATTTAA AAAGCAGCAT GTTTGTAGGG CAGCAAAACG CGGTATTTTG        60

TTTCAATTGA AAAAAAAAAG GCTTTGTTAA AAAAATTATT ATTAGTTTTA ATGAAGCAAA       120

ATATTAAGGA TCCAAATTTA TTAAAAAACA ATAAATTGTT TTAACCATAA AACCGTGTGA       180

CAGGTGCAAC TGATTAGCGA GCAGATGATT ATTCATAAAT AAATTAATGA TTGTGATTGG       240

GCACAGATGT TATTAGTCTT ATTATGGCTT AATTAGGAGT CTTATAGTCC TATAGATTAT       300

GACACCATGT TCTTTGTTAT TATTATTCTT TTAACACCAC AAACATCAAA CATTATTTAA       360

TTATTGCAAT TTATGTGGAG GGAGAAAAAA AGCTAGAAAA TGAAAAAAAA AAAAAAAGGA       420

AAAAAGAGTG CAGACTATAC GTACCAACTA TATATATGCA AATATTCTCC AGCCTGCTTG       480

AAAATAAATA ATCTGAAAAT TCACTCACT AAAAATAATA GTCCTTTGGA CAATTAAAAC        540

TAAATTAATT TTTTAAAACA ATATTTATGA TGTCGATTTA AAAATCAAGT GAATAATAAT       600

AATTATTAAA TTAGTCATTT TAAAATAAAT TTTACATTCT ACGTGTATAT ATAAAATATA       660

ACTTGATATA GTGGTAAATA GATTTTTTAT AAATTCATAT AAGGGCATAA AAGTATACAA       720

CACTATTAAA TTATTAATGT ATCGAAACAT TTACTTTTAT TTAATTTTTA AAAAAAATCA       780

TAAATTATTG ACAAAATGAA CTAATCTTAT ATCAACACGC GTTGGTACGG TATTACTAAT       840

TAAGTTCCAT TACCTTTCCA ACATGTAAGT CAAGGCAGAG GTCCCCAACT ATTTTACTAG       900

CTCCGCTCAT AGTTCCAAGT CCTGCCAACG TTTGGTATTC TTGTAAGAAT CACGACTTTG       960

GCCTGTTGTT TTCGTCTTTC ACTGTCATGT CAATACGATT TACGAAAACT ATAGGTTTAT      1020

CTTTTAAAAA CTATTTATTT TATTTATCTT TTGAATGTAT AATAGAGGGA TGGCAGTTTT      1080

TCCAAGGGAG AGTATCTTTT TCATTAGGGT AGGTTTTCTA GCAGTGGTTT AAGGTATTTC      1140

CTTTTAAGAT GTTATAAAAG AAATATTTCC GTAATAATAT TTTTTTTATC TAAGTTCACT      1200

CGTAATATTA ATTTACTCAA AATTTTATAA TAATAAATAT TATTATTAAA TGCGTGTTGA      1260

ATACATATAA GTTAATTAGG TTTAGGAAAG AAAACATAAA GGATGAAAAT GTTGAATGAA      1320

AATTTAGATG GCCGGTGAGT TAAAGAGTTG GGTCAATCAG GGCCTAATGA GGGTTTGGCA      1380

TTTTCTGGAT GGAAAGCTAA GCAGGTTGAT GGCACTTCCC ATGCAGCAGT CTTCATAGAA      1440

```
CCCACCTATA CTATATATAT ACACACTCCA CTACGGCTCT CATCTCATCT CTAAATCAAA      1500

CATTATAATA ATAACAATAA TTCTCTCTGT TTCTCTGGTT TAAACATGGG TATGGGTTTA      1560

AGGAATGGAT TTCTTTTGAT TTTATCTTGT GTTGTTACAC TTT                       1603
```

(2) INFORMATION FOR SEQ ID NO: 12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 12:

```
CAAGGAAAGT GGCAGGTCG                                                  19
```

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 13:

```
CATCCAACTT GTTCTCGACC                                                 20
```

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 14:

```
AGAGGGAAAG TGTAACAACA CAAG                                            24
```

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 15:

```
AAAGGCAGTA TTTGTTCGGA CGTG                                            24
```

(2) INFORMATION FOR SEQ ID NO: 16:

(i) SEQUENCE CHARACTERISTICS:
        (A) LENGTH: 1139 base pairs
        (B) TYPE: nucleic acid
        (C) STRANDEDNESS: double
        (D) TOPOLOGY: linear (ii) MOLECULE TYPE: Genomic DNA (iii) ORIGINAL SOURCE:
        (A) ORGANISM: Gossypium hirusutum (F) TISSUE TYPE: leaf (iv) IMMEDIATE SOURCE:
         (B) CLONE: Gh10

(vi) SEQUENCE DESCRIPTION: SEQ ID NO: 16:

CTAAGCTTTC CAAATAACCA ACAAAAAGAG CCCACCCATG CCATAATCTC CTATTTGTCA      60

TGTCTCTTTT TTAAACTCTC TCACAGTTGC AACAACCAAA CAAAGCCTCC TTCAAAATCC     120

CCGAACTGAA CTTAAAAAGT AAGTGCATAA CAGTCCCTTC CTTTTTCCAC AAAATTTACA     180

ACAACGGCTA GTTCTAACTT TCCTTCTCCA CATGTTCAAA TTAGTAGCAA TCGCATTATT     240

ACATGATCTC CACAAAAAAA CTCCTGACCT TAGGTGGAGT CTTCAAATTC CAGTTCACCT     300

TCCATATAGT AGATCGCTGA CAATCCATGT TACTATTACT ATGACCCTCC ATCCTTGCAA     360

CAATGTACCC TGATTTCACC GAGTATTACC CTACACTAAA CAATCATGAC CACCACTAAA     420

ATAAAAAGGT ATCTTCAAAA TAGCATTACA TTGTTCATCA TCATCAAGCC ATTCCTTAAT     480

ACCATCCATA TCAGTAATCT CGGTTATTAT TTGTGGCCTA CCAGACACAT CCTCTTCACC     540

ATTAGCAAAA ACAGAACCTC CTAATCTTGG AATCCATCTA TCTCTCCAAA TATTCATTGA     600

TTCTCCATTC CCTATTTGCC AATGATATCA GATCCCTTCC TGCCAAAAGA CTACTCCAAA     660

TCCATGATGC TTGTGCACCT TTTTGAGCCT CAAAGAACTC AGATTTGGAA ATATCTCCCT     720

TTCAGCACTC TAATCCAAAG GTTATCAGAT CCATTAACAA ACACCAACT TTCTTAATTC      780

TTTAAAACCC AATCCACCAT CACCCTATGT CTTAGTTAAT TTTTCCCAAC ACAACTAATG     840

AATCTTTCTT TTCCCATCCC TTTGTTCCCA AATAAAGTTG CCATATAATT ACATTATTAC     900

GGCACCTTAA ATAGAAATGG CCAAATTTGG TCGTGTGCCG TCAAGGGTCC GCGTAACGCC     960

ATTAATAAAT GAGCAAATAA ACACCCCCCC CCAAAAGGAG AGAAACCTCT CTTTCATTCT    1020

CAATATCACA AATCCTCCTA TAAAAACCAA ACTCCTAAAC CCTCATACTC CACTCCACTC    1080

ATCTTCGGTC TCTCCGCCGT TTCGCATTTC GTCTTTCTCT CTCCAATGGC TTCTATTGC     1139

(2) INFORMATION FOR SEQ ID NO: 17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 17:

GTTTGGCAGC ACAGCAGATC TGCAAGCGAG C                                    31

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 18:

GCAGAACTTC TTGAGAAGCT GTGCAGTGAG                                      30

(2) INFORMATION FOR SEQ ID NO: 19:

(i) SEQUENCE CHARACTERISTICS:

-continued

```
        (A) LENGTH: 32 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 19:

TCAACCCGGA AACACTGCCT TTAGCAAAGG GG                                        32

(2) INFORMATION FOR SEQ ID NO: 20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 20:

GTTTAATCAA GCTGCATATC TCGGTTGAGG G                                         31

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Other nucleic acid synthetic DNA (vi) SEQUENCE DESCRIPTION: SEQ ID NO: 21:

GCAATAGAAG CCATGGGAGA GAG                                                  23
```

COTTON PLANT PROMOTERS

Japanese national applications 008816/1997, 020638/1997, and 020639/1997, filed respectively on Jan. 21, Feb. 3, and Feb. 3, 1997, including all text, tables, figures, claims, nucleotide or amino acid sequences thereof, and the like, are hereby incorporated by reference in their entirety, as if fully set forth below.

FILED OF INVENTION

The present invention relates to plant promoters, i.e., nucleotide sequences having promoter function in plants. More particularly, it relates to plant promoters that control the expression of cotton fibers or the like in cotton plants. These nucleotide sequences having promoter function can also control the expression of foreign genes in eucaryote or procaryote organisms.

BACKGROUND OF THE INVENTION

The term "promoter" as used herein refers to a signal on DNA for initiating the synthesis of mRNA with the DNA as a template, and it has a common sequence of characteristic nucleotides. In particular, DNA of eucaryote organisms has a common sequence designated "TATA box" about 20 nucleotides upstream from the initiation site for transcription, and this site is believed to be a necessary site for the initiation of transcription. For the purpose of producing a desired protein in large quantities, the use of a stronger promoter is believed to be advantageous. In general, 35S promoter of cauliflower mosaic virus (CaMV) has been frequently utilized in plants because of its high activity. This promoter has been actually used for producing herbicide-resistant plants or virus-resistant plants. However, 35S promoter has little tissue specificity, so that it may be requested to have tissue specificity depending upon the purpose of use. As a promoter having plant tissue specificity, many studies have been made on cis and trans factors. The use of a promoter having plant tissue specificity makes it possible to produce a transformed plant capable of controlling the expression of an introduced gene in a desired organ. At the present time, cotton fibers are produced by cultivating a cotton plant of the genus Gossypium and collecting the cotton fibers from the capsules (cotton balls) formed on the cotton plant. The cotton fibers are characterized by various physical properties among which fiber length, fineness, and strength are particularly important. Many efforts have been made in the past to improve the characteristics of cotton fibers. In these days, the development of gene engineering has given a possibility that the fiber characteristics can be altered by the transformation of cotton plants. In this case, it is very important to express a desired gene at a desired time in a desired tissue. Under the existing circumstances, however, the mechanisms of cotton fiber formation and elongation have not yet been fully elucidated, and the related genes or promoters have not yet been clearly revealed. In order to express a desired gene in a desired tissue or at a desired time, it is desirable to use a promoter with higher tissue or time specificity rather than a promoter always involved in the expression, such as CaMV 35S promoter. In particular, such a promoter is requisite for the improvement of cotton fibers.

Cotton fibers are elongated epidermal cells of ovules, and one fiber is made of one cell. The fibers are formed by the steps of initiation, elongation, secondary wall deposition, and maturation. In the past, several cotton plant-derived promoters have been found and reported to be useful for the improvement of fiber characteristics (see International Patent Publication No. WO 94/12014). For example, E6 promoter and B8 promoter were disclosed. In particular, detailed studies were made on the E6 structure gene, showing that E6 mRNA is strongly expressed in the fibers on the 15th day or later after the flowering. Northern blotting was long exposed to the mRNAs of various tissues with a probe derived from E6 cDNA, and weak signals were obtained in flowers, ovules, and leaves (Proc. Natl. Acad. Sci. USA 89, 5769–5773, 1992; in particular, see FIG. 1 of this reference). Furthermore, FbL2A promoter has been shown to be strongly expressed in the cotton fibers on the 25th day to the 30th day after flowering (Plant Physiol. (1996) 112:1331–1341). The strength and functioning time of promoters have been known to vary with the kinds of promoters. In the formation of cotton fibers, however, the 15th day or later after flowering corresponds to the later stage of fiber elongation; therefore, the improvement of fiber characteristics is not fully achieved only by these promoters, and it requires another promoter functionable within a period of from just after flowering to the 15th day after flowering. Even if it is a promoter functionable in any other tissue than cotton fibers, i.e., promoter with lower tissue specificity, it may be useful for this purpose.

OBJECTIVE OF THE INVENTION

An objective of the invention is to provide promoters useful for the improvement of cotton fiber characteristics. Another objective is to provide transformed plants by expressing a desired gene in a desired tissue or organ, even if in any other plant than cotton plants.

SUMMARY OF THE INVENTION

Under these circumstances, the present inventors have intensively studied to improve the cotton fiber characteristics or to increase the productivity of cotton fibers, and they have already succeeded in isolating several cDNAs from cotton fibers (see U.S. Ser. Nos. 08/391,696 and 08/580,545, and the corresponding Japanese Patent Application No. 8-31987/1996). They have further studied the time- and tissue-specific expression of these isolated cDNAs and also made an experiment for cloning and subsequent analysis of the upstream sequences for these genes KC03, KC18, KC22, and Gh3, and they have found several plant promoters useful for improving the cotton fiber characteristics or increasing the productivity of cotton fibers, thereby completing the present invention.

Thus, the present invention provides plant promoters comprising DNA (a), (b), or (c) as defined below:
- (a) DNA having the nucleotide sequence of SEQ ID NO:1, 6, 11, or 16;
- (b) DNA having a nucleotide sequence modified by deletion, substitution, or addition of one or more nucleotides in DNA (a) and being capable of acting as a plant promoter;
- (c) DNA that hybridizes to DNA (a) under stringent conditions and is capable of acting as a plant promoter.

The present invention further provides plant expression vectors prepared by introducing the plant promoters into appropriate vectors; transformed plant cells prepared by introducing the plant expression vectors into host plant cells; transformed plants regenerated from the transformed plant cells; and plant seeds obtained from the transformed plants.

The present invention further provides processes for producing plants, comprising the steps of: introducing plant expression vectors containing the above plant promoters into host plant cells to cause transformation, resulting in transformed plant cells; regenerating transformed plants from the transformed plant cells; obtaining plant seeds from the transformed plants; and producing plants from the plant seeds.

DETAILED DESCRIPTION OF THE INVENTION

Figure 1:
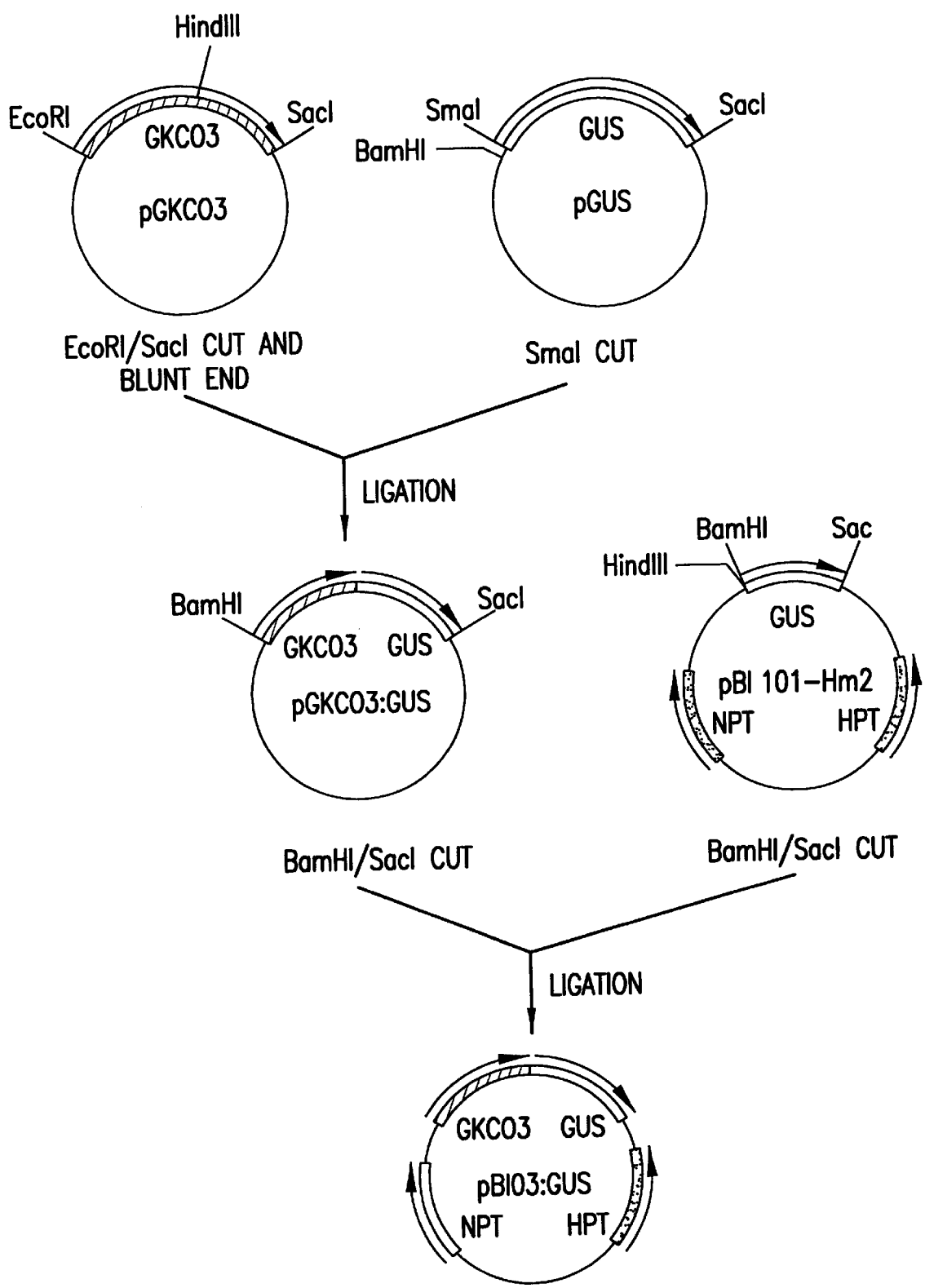
FIG. 1 is a diagram showing the construction of transformant *Escherichia coli* JM109/pBIO3:GUS.

The term "plant promoter" as used herein refers to DNA capable of acting as a promoter (i.e., having promoter function) in plants. The term "promoter" as used herein refers to a specific nucleotide sequence on DNA, which initiates the synthesis of mRNA (i.e., transcription) with the DNA as a template. The promoter has a common sequence of nucleotides, and RNA polymerase recognizes the nucleotide sequence and synthesizes mRNA. The term "promoter function" as used herein refers to a function that RNA polymerase binds to a specific region on DNA and initiates the transcription.

More particularly, the plant promoters of the present invention contain DNA (a), (b), or (c) as defined below:

(a) DNA having the nucleotide sequence of SEQ ID NO:1, 6, 11, or 16;

(b) DNA having a nucleotide sequence modified by deletion, substitution, or addition of one or more nucleotides in DNA (a) and being capable of acting as a plant promoter;

(c) DNA that hybridizes to DNA (a) under stringent conditions and is capable of acting as a plant promoter.

For the purpose of obtaining the plant promoters of the present invention, the upstream region for the gene KC03 being expressed in cotton fibers and having homology to the extensin gene of tomato was cloned by the present inventors. In the past, Northern blotting of mRNAs of various tissues with a probe derived from KC03 cDNA gave a signal in the ovules on the 10th day after flowering and also gave stronger signals in the seedlings and leaves; therefore, a promoter was expected to be present in the upstream region for the gene KC03 in these tissues. In fact, a plant promoter (GKC03) having the nucleotide sequence of SEQ ID NO:1 was isolated from a cotton plant of the genus Gossypium. The plant promoter, which is present upstream the gene KC03, makes possible the control of expression in the cotton fibers at the stage of their elongation and also in the seedlings.

Furthermore, the upstream region for the gene KC18 giving strong signals in the ovules and developing fibers in the Northern blotting was cloned by the present inventors. In the past, Northern blotting of mRNAs of various tissues with a probe derived from KC18 cDNA gave a strong signal in the ovules on the 10th day after flowering and also gave the strongest signal in the fibers on the 14th day after flowering, but no signal in the fully matured seeds, seedlings, or leaves; therefore, a quite specific promoter functionable at the stage of fiber elongation was expected to be present in the upstream region for the gene KC18. In fact, a plant promoter (GKC18) having the nucleotide sequence of SEQ ID NO:6 was isolated from a cotton plant of the genus Gossypium. The plant promoter, which is present upstream the gene KC18, makes possible the control of expression in the cotton fibers at the early stage of their elongation.

Furthermore, the upstream region for the gene KC22 giving a strong signal in the ovules on the 10th day after flowering in the Northern blotting was cloned by the present inventors. In the past, Northern blotting of mRNAs of various tissues with a probe derived from KC22 cDNA gave the strongest signal in the ovules on the 10th day after flowering, decreasing in its intensity with the progress of maturation in the ovules, and also gave a slight signal in the seedlings, but no signal in the fully matured seeds or leaves; therefore, a promoter functionable at the stage of fiber elongation was expected to be present in the upstream region for the gene KC22. In fact, a plant promoter (GKC22) having the nucleotide sequence of SEQ ID NO:11 was isolated from a cotton plant of the genus Gossypium. The plant promoter, which is present upstream the gene KC22, exhibits the control of expression in the cotton fibers at the early stage of their elongation.

Furthermore, the upstream region for the gene Gh3 being expressed in cotton fibers and having homology to the acyl carrier protein gene was cloned by the present inventors. In the past, Northern blotting of mRNAs of various tissues with a probe derived from Gh3 cDNA gave a signal in the ovules on the 2nd day after flowering, increasing to a peak on the 6th day to the 8th day after flowering, but almost no signal in the cotyledons, roots, stems, leaves, or ovules from which fibers had been removed; however, in the transformed cotton plant containing a chimera gene construct prepared by combining promoter Gh10 of the present invention with GUS gene as a reporter gene, GUS activity was observed in the fibers and even in the styles, anthers, petals, and leaves. Such a difference in expression pattern between the Northern blotting and the transformant containing the promoter-:GUS construct may be due to the modification of gene Gh3 after the transcription. The region controlling the tissue specificity may possibly be present further upstream. The plant promoter Gh10 having the nucleotide sequence of SEQ ID NO:16 was isolated from a cotton plant of the genus Gossypium and exhibits promoter function in the cotton fiber tissue at the stage of their elongation. The plant promoter, which is present upstream the gene Gh3, makes possible the control of expression even in the young developing tissues such as styles and anthers.

The plant promoters of the present invention may be DNA having a nucleotide sequence modified by deletion, substitution, or addition of one or more nucleotides in the DNA having the nucleotide sequence of SEQ ID NO:1, 6, 11, or 16, and may act as a plant promoter.

The plant promoters of the present invention may include those prepared by adding a nucleotide sequence for increasing the translation efficiency or any other purpose to the 3'-terminus of the nucleotide sequence of SEQ ID NO:1, 6, 11, or 16; and those prepared by deleting some nucleotides at the 5'-terminus of the nucleotide sequence of SEQ ID NO:1, 6, 11, or 16 so as not to lose the promoter function.

The plant promoters of the present invention may be DNA that hybridizes to the DNA having the nucleotide sequence of SEQ ID NO:1, 6, 11, or 16 under stringent conditions and is capable of acting as a plant promoter. The stringent conditions mean that hybridization is effected with 2×SSC (300 mM NaCl, 30 mM citric acid) at 42° C.

The term "plant expression vector" as used herein refers to a vector containing a plant promoter as described above. The appropriate vector which can be used may include *E. coli* derived vectors, e.g., pGEM-T vector; β-glucuronidase (GUS) gene-containing plasmids, pBI101-Hm-2, shuttle vectors, helper plasmids, and pRK2013. Also utilized are plant viruses, e.g., cauliflower mosaic virus (CaMV). The vector may be selected depending upon the kind of host cell.

The plant promoter can be introduced into a vector by a method for introducing an ordinary gene into a vector.

The term "transformed plant cell" as used herein refers to a transformed plant cell that has been prepared by introducing a plant expression vector as described above into a host plant cell. The host plant cell may be those of *Arabidopsis thaliana*, tomato, tobacco, petunia, wheat, rice, corn, pumpkin, cucumber, or cotton.

The plant expression vector can be introduced into a host plant cell to cause transformation by a method such as electroporation, protoplast fusion, microinjection, polyethylene glycol method, or particle gun method.

The term "transformed plant" as used herein refers to a transformed plant that has been regenerated from a transformed plant cell as described above. The transformed plant can be regenerated, for example, by a method in which transformed cells in callus form are transferred to various media containing hormones in different kinds and concentrations, and then cultivated to form adventive embryos, from which whole plants are obtained. The media which can be used may include MSIC media (MS salts, 0.75% MaCl$_2$, 1.9 g/l KNO$_3$, 30 g/l glucose, 2.0 g/l Gellan gum; pH 5.8) for cotton, and Kamda & Harada media for carrot.

The "process for producing a plant" of the present invention comprises the steps of: introducing a plant expression vector containing a plant promoter as described above into a host plant cell to cause transformation, resulting in a transformed plant cell; regenerating a transformed plant from the transformed plant cell; obtaining a plant seed from the transformed plant; and producing a plant from the plant seed.

The term "step of obtaining a plant seed from the transformed plant" as used herein refers to a step in which the transformed plant is transferred from a rooting medium to a pot filled with water-containing soil, followed by cultivation at a constant temperature, and the transformed plant is grown so that flowers come out and seeds arc finally formed.

The term "step of producing a plant from the plant seed" as used herein refers to a step in which the seeds formed and matured on the transformed plant are isolated and then sowed in water-containing soil, followed by growing at a constant temperature under illumination, resulting in a plant.

The plant promoters of the present invention can be obtained, for example, by the following steps.

(1) Cloning of upstream region for cotton fiber tissue-specific gene (2) Fusion with β-glucuronidase (GUS) gene (3) Introduction of plasmid into Agrobacterium (4) Regeneration of transformed plant (5) Determination of GUS activity Each of these steps will hereinafter be further explained in detail.

<1>Isolation of Promoter Regions for Genes Involved in Cotton Fiber Formation and Elongation Based on the nucleotide sequences of tissue-specific genes KC03, KC18, KC22, and Gh3 obtained from cotton fibers (see U.S Ser. Nos. 08/391,696 and 08/580,545, and the corresponding Japanese Patent Application No. 8-31987/1996), synthetic oligonucleotides are prepared for the inverse PCR method. That is, genomic DNA is extracted from cotton fibers and then digested with an appropriate restriction endonuclease(s). The resulting fragments are self-ligated, and the ligated DNA is used as a template of PCR. The PCR is effected with the first group of primers, and the reaction products are further subjected to subsequence PCR with the second group of primers, followed by cloning of the upstream region.

A clone having a desired length is obtained by agarose gel electrophoresis and then subcloned into TA cloning vector, followed by the determination of a nucleotide sequence. The nucleotide sequence of the PCR fragment obtained has completely the same part as the nucleotide sequence of KC03, KC18, KC22, or Gh3, and it is, therefore, found that this part is present upstream the gene KC03, KC18, KC22, or Gh3.

<2>Utilization of Promoter Regions for Genes Involved in Cotton Fiber Formation and Elongation The plant promoters obtained by the above method can be utilized for controlling the expression of proteins associated with the cotton fiber formation and elongation by preparing a chimera gene construct in cotton or other plants. Furthermore, when combined with a DNA sequence coding for the signal peptide, the plant promoters can be utilized for modifying the components of a cell wall by expressing various proteins in the cell wall. These plant promoters can also be applied to the development of novel varieties of plants with disease resistance.

For example, a gene involved in the cotton fiber formation and elongation is ligated to the plant promoters of the present invention and then introduced into cotton or other plants, so that the content of a desired protein can be increased. In contrast, at least a part of the minus strand (i.e., complementary sequence to the coding sequence) is ligated in reverse direction to the plant promoters of the present invention and then introduced into a plant, followed by expression of so-called anti-sense RNA, so that the content of a desired protein can be decreased.

<3>Introduction of Plant Promoters Into Appropriate Vectors and Transformation of Host Plant Cells The plant cells can be transformed by an ordinary method such as electroporation in which protoplasts are treated with electric pulses to introduce plasmids into the plant cells; fusion of small cells, cells, lysosomes, or the like with protoplasts; microinjection; polyethylene glycol method; or particle gun method.

A desired gene can be introduced into a plant by making use of a plant virus as a vector. The plant virus to be used may include cauliflower mosaic virus (CaMV). That is, a virus genome is previously inserted into an *E. coli* derived vector to prepare a transformant, and the desired gene is inserted into the virus genome in the transformant. The virus genome thus modified is digested from the transformant with an appropriate restriction endonuclease and then introduced into a plant, so that the desired gene can be inserted into the plant (see, e.g., Hohn et al., Molecular Biology of Plant Tumors, Academic Press, New York, pp. 549–560 (1982); and U.S. Pat. No. 4,407,956).

Furthermore, there is a technique using a Ti plasmid of Agrobacterium. When a plant is infected with bacteria of the genus Agrobacterium, a part of their plasmid DNA is transferred to the plant genome. By making use of such a property, a desired gene can also be introduced into a plant. Upon infection, for example, *Agrobacterium tumefaciens* and *Agrobacterium rhizogenes* induce the formation of crown galls and the formation of hairy roots, respectively. Each of these bacteria has a plasmid designated "Ti-plasmid" or "Ri-plasmid" having T-DNA (transferred DNA) and vir region. The tumor formation is caused by incorporation of T-DNA into the genome of a plant, and then transcription and translation of an oncogene present in the T-DNA in the plant cells. The vir region per se is not transferred to the plant cells, but it is essential to the transfer of T-DNA. Also, the vir region can function even if it is on another plasmid different from the T-DNA containing plasmid (Nature, 303, 179 (1983)).

If a desired DNA is inserted in the T-DNA on the Ti- or Ri-plasmid, the desired DNA can be incorporated into the plant genome upon infection of the plant with the bacteria of the genus Agrobacterium. In this case, a portion inducing the formation of crown galls or hairy roots is removed from the T-DNA of the Ti- or Ri-plasmid without deteriorating the desired transfer function, and the plasmid thus obtained can be used as a vector. In the present invention, various vectors including such a vector can be used. For example, a vector designated "binary vector" such as pBI101 (Clontech, Co.) can be used as follows: The gene involved in the fiber formation and elongation is ligated in sense or anti-sense direction to the plant promoters of the present invention, and then inserted in the binary vector, followed by introduction into a plant cell. The binary vector has no vir region, and the bacteria of the genus Agrobacterium used for the introduction of the vector are, therefore, required to contain another plasmid having vir region.

These vectors serve as a shuttle vector that can be amplified in *E. coli* as well as in the bacteria of the genus Agrobacterium. Recombination with a Ti-plasmid can, therefore, be carried out with *E. coli*. In addition, these vectors contain antibiotic-resistance genes, so that transformants can readily be screened in the transformation of *E. coli*, bacteria of the genus Agrobacterium, plant cells, or the like. These vectors further contain 35S promoter of cauliflower mosaic virus (CaMV), so that the gene inserted in these vectors can be incorporated into the plant genome and then expressed under no regulatory control.

<4>Regeneration of Plants From Transformed Plant Cells

The following will illustrate the introduction of a desired gene into host plant cells by Agrobacterium infection and the regeneration of plants from the transformed cells in the case of *Arabidopsis thaliana*.

The seeds of *Arabidopsis thaliana* are sowed and aseptically cultivated according to an ordinary method. The cut pieces of a rooting hypocotyl are used to prepare a callus culture. A desired gene is ligated to the plant promoters of the present invention and then inserted in a plasmid having antibiotic-resistance genes. The resulting plasmid is transformed into Agrobacterium, followed by preparation of a bacterial culture. The cut pieces of the hypocotyl in callus form are cocultivated with the bacterial culture. When the bacteria are grown enough to be observed by the naked eye, the bacteria on the cut pieces are sterilized and then further cultivated. The transformed cut pieces are continuously grown, and the appearance of calli will be observed. Because of the screening with antibiotics, non-transformed cut pieces turn brown in color. The cultivation is continued until the transformants have a size of about 5 mm to form shoots. When the transformants have taken the form of complete shoots, they are transferred to a rooting plate. After rooting, they are transplanted on a rock wool.

The rooting plant is transplanted in the soil soaked with inorganic salts medium and then grown to give seeds. The seeds are sterilized, sowed, and then germinated, thereby obtaining a transformed plant. From this transformed plant, DNA is extracted according to an ordinary method. This DNA is digested with appropriate restriction endonuclease (s), and the resulting fragments are subjected to Southern hybridization by the use of a gene involved in the fiber formation and elongation as a probe. Thus, it can be confirmed whether transformation has occurred in the plant.

The following will illustrate the introduction of a desired gene into host plant cells by Agrobacterium infection and the regeneration of plants from the transformed cells in the case of cotton plants of the genus Gossypium.

The transformation can be carried out by the method reported by N. Trolinder et al. (Theor. Appl. Genet. (1992) 83:645–649). The seeds of a cotton plant are sterilized and then germinated. The hypocotyls are infected with Agrobacteirum, and the continued cultivation gives calli within several months. The calli are further grown to a diameter of about 1 cm, and a suspension culture is prepared. The embryos are matured to a size of about 1 cm and then grown in a culture tube. After growth to a certain extent, they are planted in soil, so that plural transformed cotton plants are finally obtained. For the resulting transformed lines, the introduction of a desired gene can be confirmed by the examination of genomic DNA using the PCR method.

From the transformants or non-transformants, RNA is extracted by an ordinary method, and probes each having a sense or anti-sense sequence of the gene involved in the fiber formation and elongation. The level of expression of a desired gene can be determined by Northern hybridization using these probes.

In the present invention, if GUS gene that has been widely utilized as a reporter gene in plants is used in the form ligated to the 3'-terminus of the plant promoters of the present invention, the strength of the plant promoter can readily be determined by the examination of GUS activity. The reporter gene may include, in addition to GUS gene, luciferase and green-fluoresceinated proteins.

The genes involved in the fiber formation and elongation are expressed in cotton fiber cells during the process of cotton fiber formation and associated with the fiber elongation. The use of upstream regions for these genes gives a possibility that the transcription factor or other factors associated with the cotton fiber elongation can be identified. The plant promoters of the present invention are, therefore, promoters involved in the cotton fiber formation and elongation, and they can be utilized for the establishment of a technique for inducing the cotton fiber formation and elongation; the isolation of cis and trans factors associated with the cotton fiber elongation; the elucidation of mechanisms of the cotton fiber formation and elongation; or the isolation of genes controlling the cotton fiber formation and elongation. Thus, the plant promoters of the present invention are quite useful in the technical field on the cell formation and elongation. The plant promoters of the present invention cause the gene expression in young developing tissues. Therefore, if a desired gene is expressed in sense or anti-sense direction in young developing tissues, an expected change is made in the level of gene expression.

Furthermore, if the nucleotide sequence coding for a protein associated with the fiber formation and elongation is ligated to the plant promoters of the present invention to form a chimera gene, the plant cell wall of a specific tissue can be changed in its structure. Therefore, the plant promoters of the present invention can be useful for the processing of plant materials to be used in the industrial field. In general, the use of 35S promoter of cauliflower mosaic virus (CaMV) makes it possible to make a change in shape all over the plant organs throughout the whole process of a life cycle. The use of a regulatory promoter for light, heat, lesions, or other factors makes it possible to produce a plant that can change its shape according to the growth circumstances. The use of an organ- or tissue-specific promoter makes it possible to give a change in shape only in the specific organ or tissue. In other words, the control of fiber formation and the change of fiber characteristics can be achieved by using the plant promoters of the present invention. The plant promoters of the present invention can also be applied to the young developing tissues of a plant.

The plant promoters of the present invention can be used to specifically express a desired gene in a specific plant tissue. In particular, a desired gene can be expressed in the young developing tissues of a plant or in the cotton fibers. For example, the expression of a desired gene in the cotton fibers using the plant promoters of the present invention makes it possible to improve the cotton fiber characteristics (e.g., fiber length, fineness, strength) and to increase the yield of the cotton fibers. The utilization of the plant promoters of the present invention makes it possible to produce novel varieties of cotton plants having more excellent fiber characteristics and higher productivity.

EXAMPLES

The present invention will be further illustrated by the following Examples; however, the present invention is not limited to these Examples.

Example 1

(1) Cloning of Upstream Region (GKC03) for Cotton Fiber Tissue-derived Gene KC03

The seedlings on the 18th day after the seeding of a cotton plant of the genus Gossypium were used to extract genomic DNA by an improved method of Murray and Thompson. The extracted genomic DNA was cloned by the inverse PCR method.

First, 1 $\mu$g of the genomic DNA was digested with restriction endonuclease Eco RI, and the resulting fragments were self-ligated with T4 ligase. Then, 500 $\mu$g of the ligated DNA was used as a template for the amplification of the upstream region for KC03 (hereinafter referred to as GKC03) with a PCR reagent kit (LA-PCR kit, Takara Shuzo, Co., Ltd.). The reaction was effected with the first group of primers having the respective nucleotide sequences of SEQ ID NOs:2 and 3, and the steps of PCR at 94° C. for 15 seconds and at 65° C. for 12 minutes were repeated in 28 cycles. The PCR products were used for the subsequent PCR with the second group of primers having the respective nucleotide sequences of SEQ ID NOs:4 and 5 under the same conditions as described above. The PCR products wereexamined for amount and length by electrophoresis. The resulting DNA fragment was introduced into the vector pT7BlueT and then cloned by the transformation of E. coli JM109. The plasmid clone thus obtained was designated pGKC03. The nucleotide sequence of GKC03 was determined with a sequenase sequence kit (Amersham Corp.). The nucleotide sequence thus determined was completely the same as that of cDNA on the basis of the primer sequences, and it was, therefore, found to be a genomic region corresponding to the cDNA. The nucleotide sequence is shown in the Sequence Listing, SEQ ID NO:1.

(2) Fusion with β-glucuronidase (GUS) gene

The plasmid pBI101-Hm2 containing β-glucuronidase (GUS) gene (furnished by Prof. Atsuhiko Shinmyo in the Nara Institute of Science and Technology) was digested with restriction endonucleases Hind III and Sac I, and the resulting fragments were subjected to agarose gel electrophoresis for the separation of the GUS gene from the plasmid. The GUS gene was inserted at the Hind III/Sac I site in the plasmid pUC19 to give plasmid pGUS.

The plasmid pGKC03 was digested with restriction endonucleases Eco RI and Sac I, and the resulting fragments were treated to have blunt ends and then inserted at the Sma I site in the plasmid pGUS. The nucleotide sequence of the Eco RI-Sac I fragment thus inserted was used for the determination of whether the fragment was correctly inserted or not. The plasmid with the correctly inserted fragment was designated pGKC03:GUS.

The plasmid pGKC03:GUS was further digested with restriction endonucleases Bam HI and Sac I, and the resulting fragments were subjected to electrophoresis. After that, the Bam HI-Sac I fragment was inserted at the Bam HI/Sac I site in the plasmid pBI101-Hm2 to give novel plasmid pBI03:GUS. E. coli JM109 was then transformed with the pBI03:GUS to give E. coli JM109/pBI03:GUS. The construction of this transformant is shown in FIG. 1.

(3) Introduction of Plasmid Into Agrobacterium

E. coli JM109/pBI03:GUS obtained in (2) and E. coli with helper plasmid pRK2013 were separately grown on LB media each containing 50 mg/l of kanamycin at 37° C. overnight, while Agrobacterium strain EHA101 (furnished by Prof Atsuhiko Shinmyo in the Nara Institute of Science and Technology) was grown on LB medium containing 50 mg/l of kanamycin at 37° C. over two successive nights.

The bacterial cells were harvested by taking 1.5 ml of each of the cultures in an Eppendorf tube and then washed with LB medium. These bacterial cells were each suspended in 1 ml of LB medium, after which three kinds of bacteria were mixed together in 100 µl portions. The mixture was plated on LB agar medium and then incubated at 28° C. for the conjugation transfer of both plasmids to Agrobacterium. After 1 to 2 days, a part of the medium was scratched with a sterile loop and then spread over LB agar medium containing 50 mg/l kanamycin, 20 mg/l hygromycin B, and 25 mg/l chloramphenicol. After incubation at 28° C. for 2 days, a single colony was selected. The transformant thus obtained was designated EHA101/pBI03:GUS.

(4) Cultivation of Sterile *Arabidopsis thaliana*

Several dozens of seeds of *Arabidopsis thaliana* stain Wassilewskija (hereinafter referred to as strain WS) (furnished by Prof. Atsuhiko Shinmyo in the Nara Institute of Science and Technology) were placed in a 1.5 ml tube, to which 1 ml of 70% ethanol was added, and the seeds were left stand for 3 minutes. After that, the seeds were immersed in a solution for sterilization (5% sodium hypochlorite, 0.02% Triton X-100) for 3 minutes, washed five times with sterilized water, and then sowed on GM plate (4.3 g/l Murashige-Skoog inorganic salts, 10 g/l sucrose, 0.1 g/l of myoinositol, 5 g/l of Gellan gum; pH 5.7). This plate was left stand at 4° C. for 2 days for low temperature treatment, and cultivation was carried out in a plant incubator (model MLR-350HT, Sanyo Electric Co., Ltd.) at 22° C. under weak light for 7 days.

(5) Infection with Agrobacterium

The hypocotyls of several plants of the above strain WS cultivated for 7 days in (4) were arranged and then cut with a surgical knife to have a uniform length of about 1.0 cm. These cut pieces were placed side by side on CIM plate (containing 3.9 g/l Gamborg B5 medium salt mixture, 20 g/l glucose, 0.1 g/l myoinositol, 5 g/l Gellan gum, 0.5 µg/l 2,4-dichlorophenoxyacetic acid, 0.05 µg/l kinetin; pH 5.7) and then cultivated in the light period of 24 hours at a light intensity of 3000 lux for 2 days. The culture of transformant EHA101/pBI03:GUS obtained in (3), which had been incubated at 28° C. for 1 day, was 3-fold diluted with MS diluent (6.4 g/l Murashige-Skoog inorganic salts; pH 6.3), and the dilution was dispensed in 1 ml portions into several tubes. The hypocotyls in callus form cultivated on CIM medium for 2 days were immersed in these tubes for 10 minutes and then placed side by side on two layers of sterile filter papers to remove excess water. About twenty hypocotyls were transferred on each fresh CIM plate and then cocultivated for 2 days under the same conditions as described above.

(6) Sterilization

The cut pieces grown to an extent enough to observe the respective bacterial strains with the naked eye were placed in a solution for sterilization (prepared by adding claforan to MS diluent to yield a final concentration of 200 µg/ml) and then washed with gentle shaking for 60 minutes. After five repetitions of this procedure, these cut pieces were placed on a sterile filter paper to remove water, placed side by side on SIM plate (containing 3.9 g/l Gamborg B5 medium salt mixture, 20 g/l glucose, 0.1 g/l myoinositol, 5 g/l Gellan gum, 50 mg/l kanamycin, 20 mg/l hygromycin B, 0.2 g/l claforan, 0.5 g/l vancomycin, 5 mg/l 2iP, 0.15 mg/l IAA; pH 5.7), and then cultivated at a light intensity of 4000 lux for 2 days.

(7) Selection of Transformed Plants

The above cut pieces cultivated for 2 days in (6) were transferred to SIM plate and then cultivated at a light intensity of 4000 lux. After that, these cut pieces were transferred to fresh SIM plate every week. The transformed cut pieces were continuously grown to become dome-shaped swollen calli, whereas the non-transformants turned brown in color. The calli of the transformants exhibited green color after about two weeks. After about one month, shoots were formed.

(8) Regeneration of Transformed Plants

Shoots were cut at their bases with a razor or a surgical knife so as not to include any callus, and slightly inserted into RIM plate (4.3 g/l MS salt, 10 g/l sucrose, 0.1 g/l myoinositol, 3.5 g/l Gellan gum, 0.02 mg/l of indolebutyric acid; pH 5.7) as if they were placed thereon. After about one month, the plant having several roots of about 1 to 2 cm in length was transplanted with a pincette in the soil prepared by mixing pearlite and vermiculite (TES Co.) at a ratio of 1:1 and soaking in an inorganic salts mixed medium. After about one month, a few hundred of seeds were obtained from each plant. These seeds are hereinafter referred to as T1 seeds.

(9) Selection of Antibiotic-resistant Strains

About one hundred T1 seeds were sterilized by the same method as described in (4) and then sowed in GM plate (containing 50 mg of kanamycin and 20 mg of hygromycin B). Kanamycin and hygromycin B-resistant strains were germinated at a ratio of approximately 3:1.

(10) Measurement of GUS Activity

Figure 2:
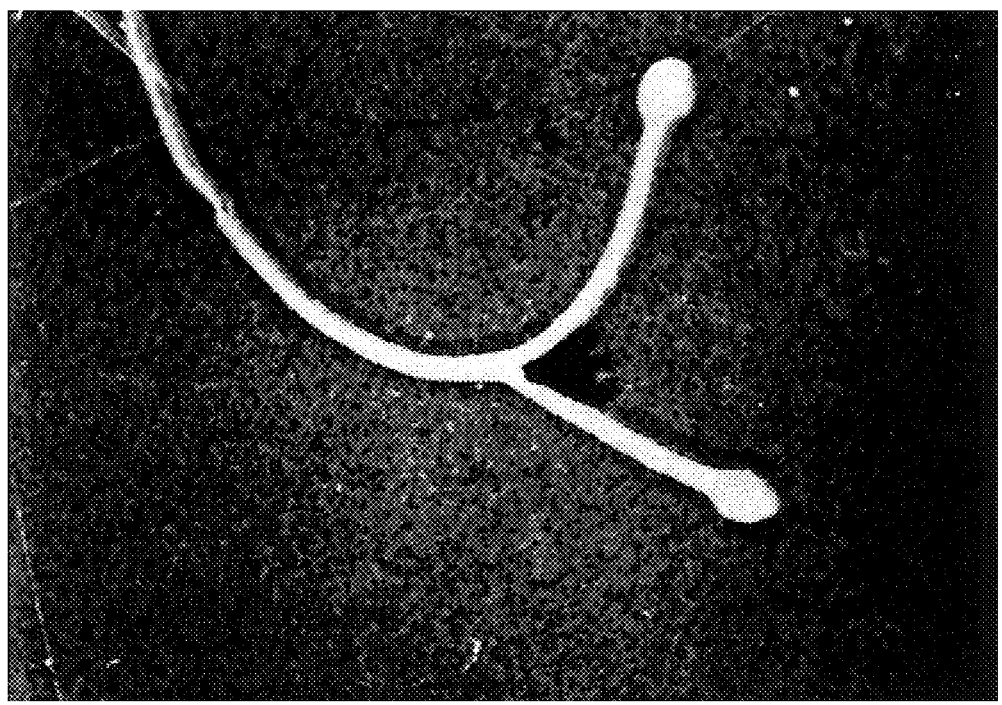
FIG. 2 is a photograph showing the GUS staining of transformed *Arabidopsis thaliana* after one-week growth in the dark.
Figure 3:
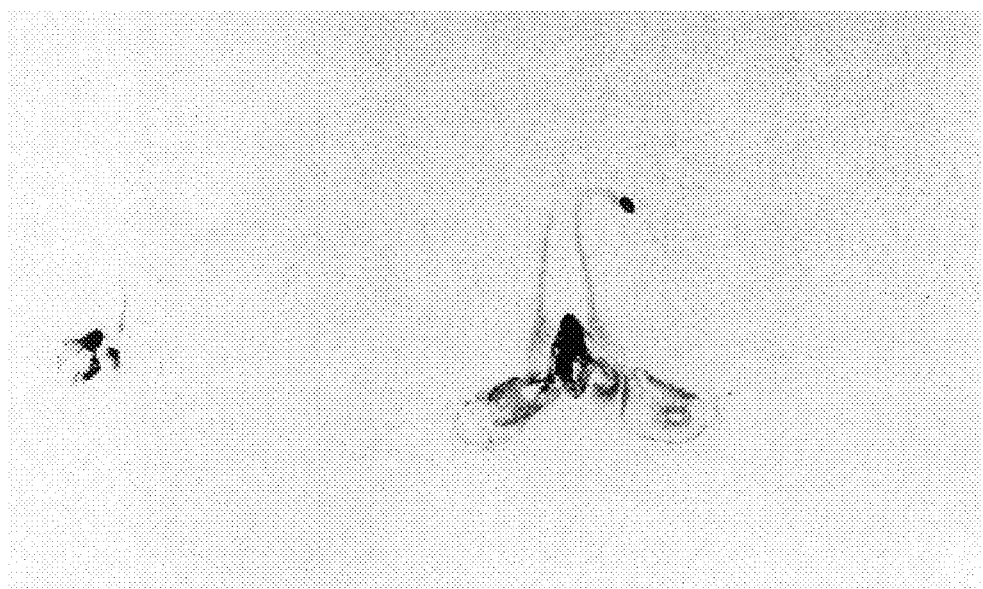
FIG. 3 is a photograph showing the GUS staining of the transformed *Arabidopsis thaliana* after three-week growth.
Figure 4:
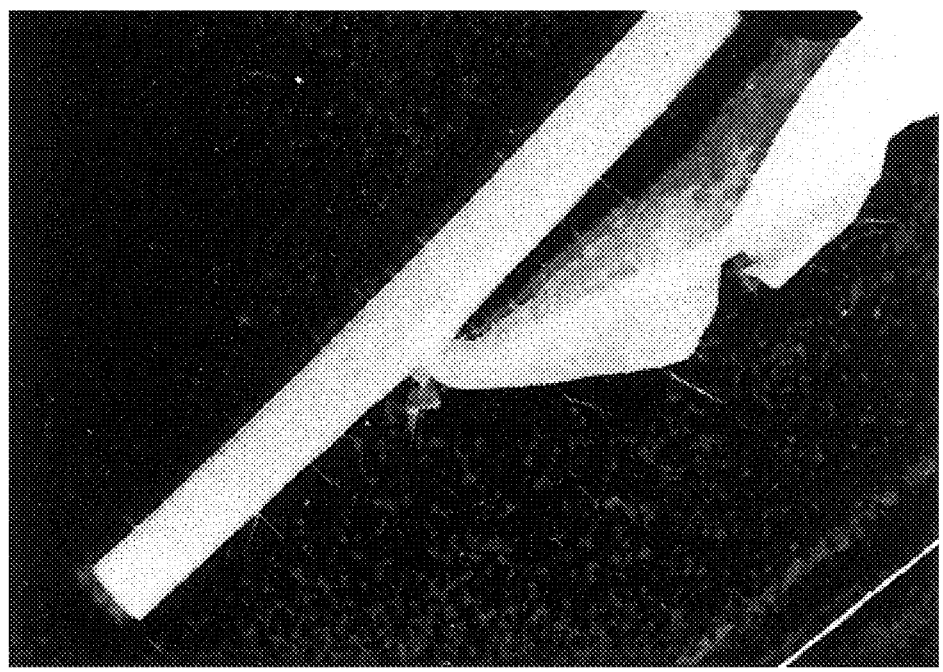
FIG. 4 is a photograph showing the GUS staining of a scape of the transformed *Arabidopsis thaliana* after seven-week growth.
Figure 5:
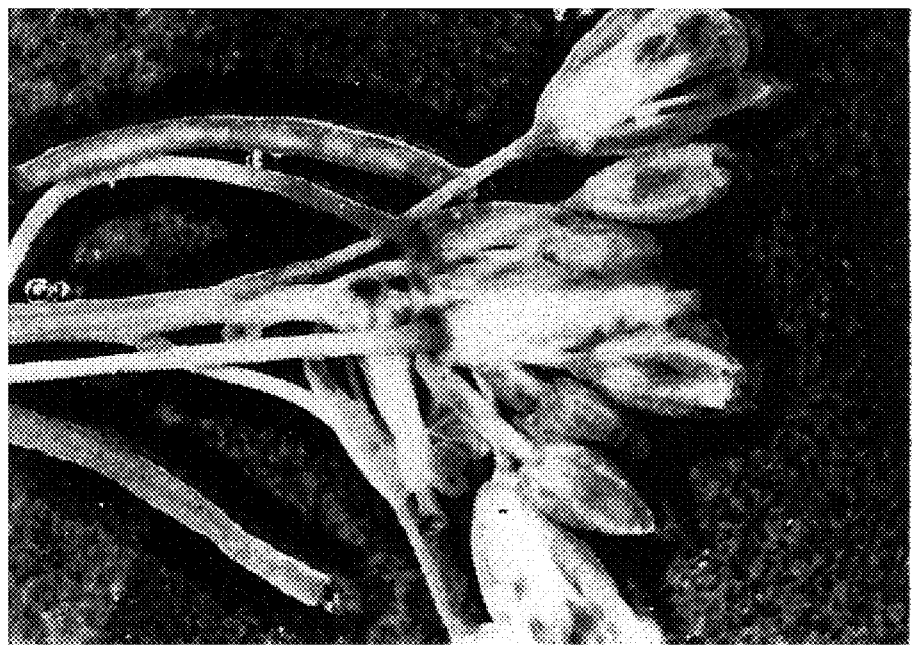
FIG. 5 is a photograph showing the GUS staining of flowers of the transformed *Arabidopsis thaliana* after seven-week growth.
Figure 6:
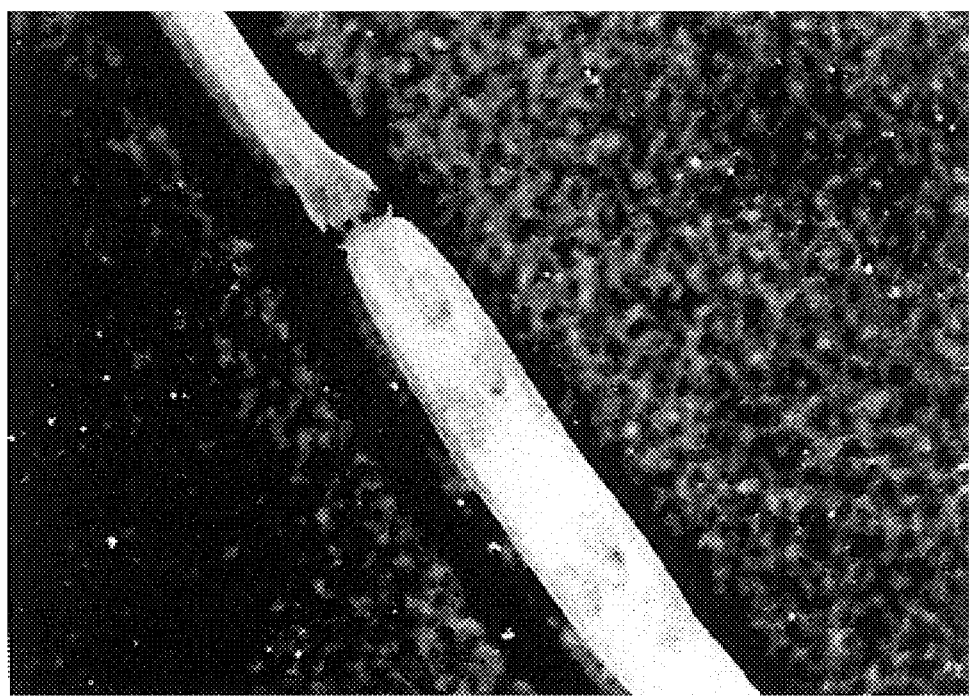
FIG. 6 is a photograph showing the GUS staining of a pod base of the transformed *Arabidopsis thaliana* after nine-week growth.

The transformed *Arabidopsis thaliana* as the homozygote obtained was cultivated. The tissues of this plant were cut with a surgical knife, and the cut pieces were immersed in several milliliters of fixing solution (0.03% formalin, 10 mM MES (pH 5.6), 0.3 M mannitol) at room temperature for 45 minutes. The cut pieces were washed several times with 50 mM phosphate buffer (pH 7.0). These cut pieces were immersed in the GUS staining solution (50 mM phosphate buffer, 0.5 M potassium ferricyanide, 0.5 M potassium ferrocyanide, 1 mM X-Gluc) and then treated under reduced pressure by suction with a vacuum pump, so that the solution was entirely absorbed into the inside of the sample, followed by overnight incubation at 37° C. For the removal of chlorophyll, the sample was immersed in 5% formalin for 10 minutes, and then immersed in 5% acetic acid for 10 minutes, in 50% ethanol for 10 minutes and in 100% ethanol for 10 hours. The blue-stained tissues were observed with a microscope, and the promoter function was confirmed even in *Arabidopsis thaliana*. In particular, strong specific expression was observed in the shoot apices of the seedlings as shown in FIGS. 2 and 3. Expression was also observed in the lateral bud as shown in FIG. 4, in the flowers on the 7th week as shown in FIG. 5, and in the pod base on the 9th week as shown in FIG. 6. These results indicate that the DNA isolated in this Example functions as a promoter with tissue specificity, even in *Arabidopsis thaliana* which is a plant other than cotton plants.

(11) Transient Assay with Particle Gun

The particle gun apparatus PDS-1000/He available from Nippon BioRad Laboratories K.K. was used.

11.1. Preparation of Gold Particle Stock

First, 60 mg of 1.0 μm gold particles was put into a 1.5 ml microtube, to which 1 ml of 70% ethanol was added, and the microtube was agitated with a vortex mixer for 5 minutes, and then left undisturbed for 15 minutes. After centrifugation at 10,000 rpm for 5 seconds, the supernatant was discarded, and 1 ml of distilled water was added to the residue. The microtube was agitated with a vortex mixer for 1 minute and then left undisturbed for 1 minute, followed by centrifugation. After centrifugation at 10,000 rpm, the supernatant was discarded, and the residue was suspended in 1 ml of 50% sterilized glycerol.

11.2. DNA Adsorption on Metal Particles

First, 50 μl of gold particle suspension was put into a 1.5 ml sterilized microtube, to which 5.0 μl of a solution of the plasmid pBI03:GUS (1.0 μg/μl) dissolved in TE buffer, 50 μl of 2.5 M calcium chloride, and 20 μl of 0.1 M spermidine were added, and the microtube was agitated for 3 minutes and then left undisturbed for 1 minute. After centrifugation at 1,000 rpm, the supernatant was discarded. The residue was washed with 70% ethanol, further washed with 99.5% ethanol, and then suspended in 60 μl of 99.5% ethanol. The suspension was applied in 6 μl to a macro carrier, followed by drying, and then used.

11.3. Discharge of Particles

The particle gun apparatus was loaded with a rupture disk and then with a stopping disk and the macro carrier. After the loading, a sample was placed in a chamber. As the sample, cotton ovules on the 2nd day after flowering, and cotton ovules, cotton leaves and cotton seedlings on the 14th day after flowering were used. The chamber was depressurized, and a helium gas valve was opened, so that the rupture disk was broken at 600 psi to accelerate the macro carrier. A stopping screen stopped the macro carrier, so that the particles were introduced into the sample.

11.4. Staining of Tissues

Figure 7:
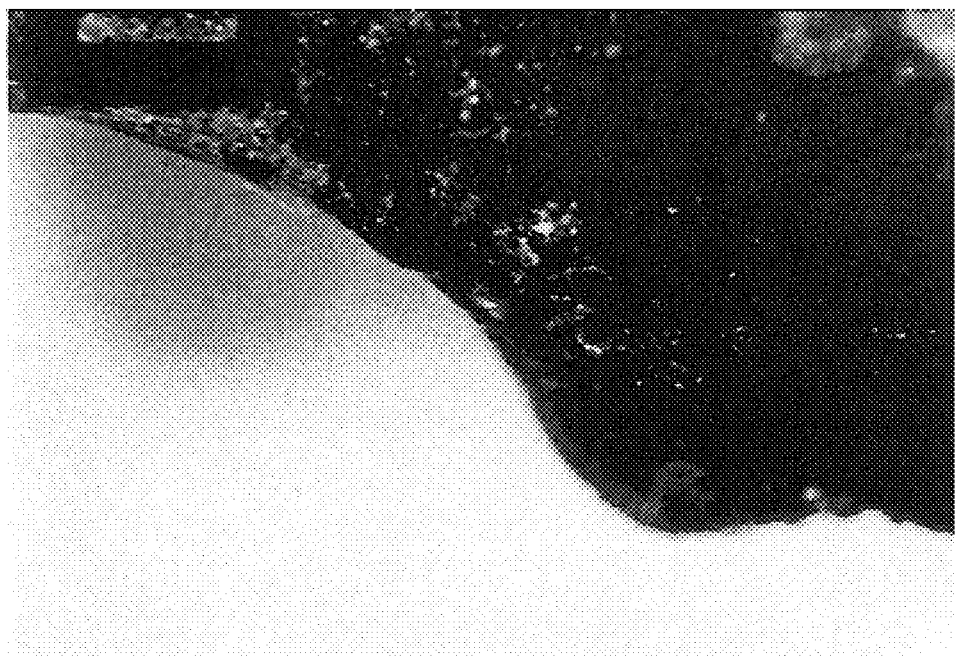
FIG. 7 is a photograph showing the GUS staining of a cotton cotyledon subjected to gene introduction with a particle gun.

The plasmid pBI03:GUS was introduced into cotyledons, and these plants were cultivated on MS agar medium for 2 days, followed by staining of cotyledon tissues. The sample was immersed in a fixing solution (0.3% formalin, 10 mM MES (pH 5.6), 0.3 M mannitol) at room temperature for 45 minutes and then washed several times with 50 mM phosphate buffer (pH 7.9). This sample was immersed in the GUS staining solution (50 mM phosphate buffer, 0.5 M potassium ferricyanide, 0.5 M potassium ferrocyanide, 1 mM X-Gluc) and then treated under reduced pressure by suction with a vacuum pump, so that the solution was entirely absorbed into the inside of the sample, followed by overnight incubation at 37° C. For the removal of chlorophyll, the sample was immersed in 5% formalin for 10 minutes, and then immersed in 5% acetic acid for 10 minutes, in 50% ethanol for 10 minutes and in 100% ethanol for 10 minutes. The blue-stained tissue was observed with a microscope, and blue spots were observed in the vicinity of a cotyledon's stem as shown in FIG. 7, indicating that the introduced gene was expressed. The observation of blue spots thus confirmed that the DNA of this Example also functions as a promoter in cotton plants.

Example 2

(1) Cloning of Upstream Region (GKC18) for Cotton Fiber Tissue-derived Gene KC18

The seedlings on the 18th day after the seeding of a cotton plant of the genus Gossypium were used to extract genomic DNA by an improved method of Murray and Thompson. The extracted genomic DNA was cloned by the inverse PCR method.

First, 1 μg of the genomic DNA was digested with restriction endonuclease Hind III, and the resulting fragments were self-ligated with T4 ligase. Then, 500 μg of the ligated DNA was used as a template for the amplification of the upstream region for KC18 (hereinafter referred to as GKC18) with a PCR reagent kit (LA-PCR kit, Takara Shuzo, Co., Ltd.). The reaction was effected with the first group of primers having the respective nucleotide sequences of SEQ ID NOs:7 and 8, and the steps of PCR at 94° C. for 15 seconds and at 65° C. for 12 minutes were repeated in 28 cycles. The PCR products were used for the subsequent PCR with the second group of primers having the respective nucleotide sequences of SEQ ID NOs:9 and 10 under the same conditions as described above. The PCR products were examined for amount and length by electrophoresis. The resulting DNA fragment was introduced into the vector pT7BlueT and then cloned by the transformation of *E. coli* JM109. The plasmid clone thus obtained was designated pGKC18. The nucleotide sequence of GKC18 was determined with a sequenase sequence kit (Amersham Corp.). The nucleotide sequence thus determined was completely the same as that of cDNA on the basis of the primer sequences, and it was, therefore, found to be a genomic region corresponding to the cDNA. The nucleotide sequence is shown in the Sequence Listing, SEQ ID NO:6.

(2) Fusion with β-glucuronidase (GUS) Gene

The plasmid pBI101-Hm2 containing β-glucuronidase (GUS) gene (furnished by Prof. Atsuhiko Shinmyo in the Nara Institute of Science and Technology) was digested with restriction endonucleases Hind III and Sac I, and the resulting fragments were subjected to agarose gel electrophoresis for the separation of the GUS gene from the plasmid. The GUS gene was inserted at the Hind III/Sac I site in the plasmid pUC19 to give plasmid pGUS.

The plasmid pGKC18 was digested with restriction endonuclease Nco 1, and the resulting fragments were treated to have blunt ends, digested with restriction endonuclease Hind III, and then inserted at the Hind III/Sma I site in the plasmid pGUS. The nucleotide sequence thus inserted was used for the determination of whether the fragment was correctly inserted or not. The plasmid with the correctly inserted fragment was designated pGKC18:GUS.

Figure 8:
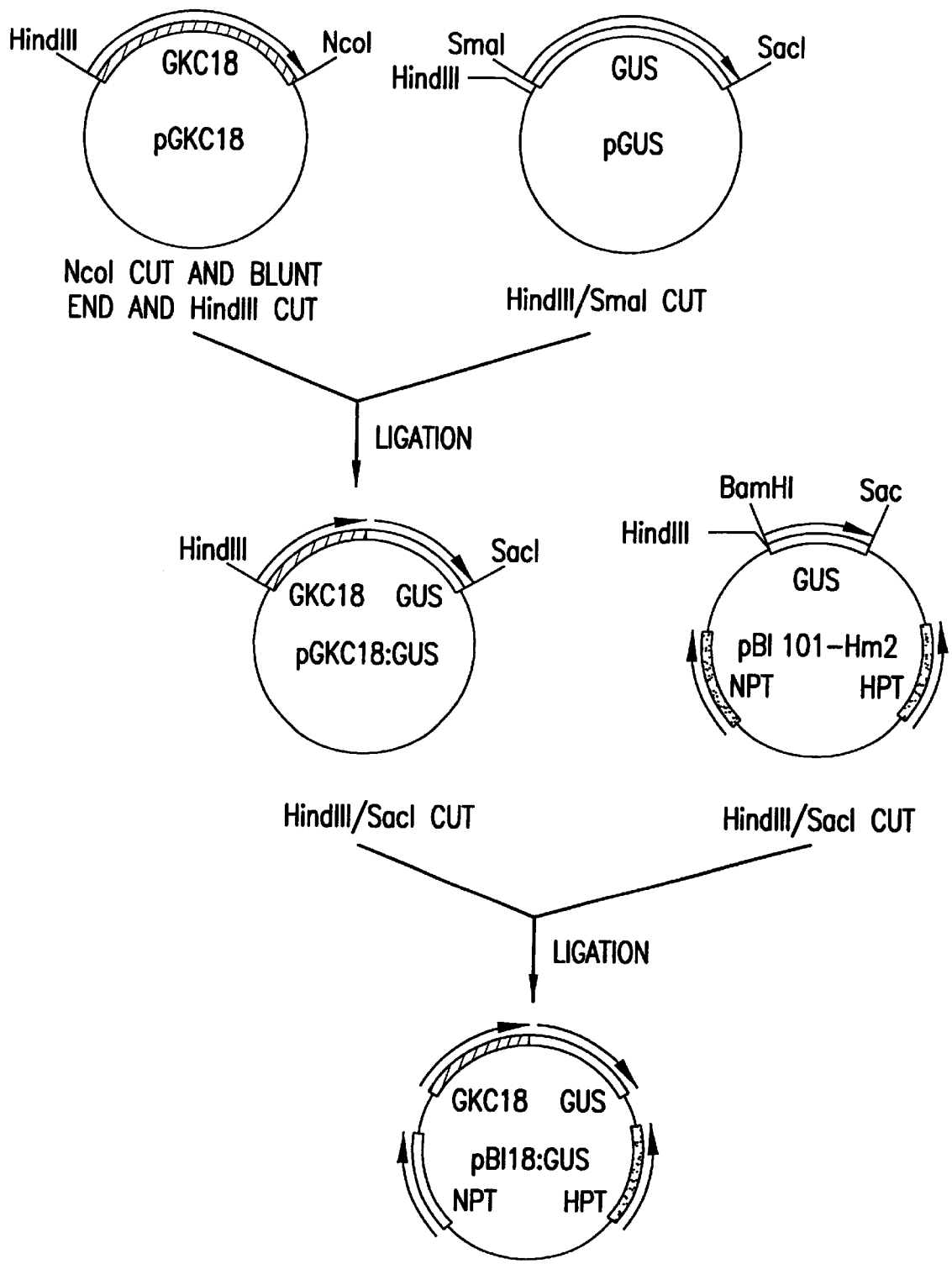
FIG. 8 is a diagram showing the construction of transformant *Escherichia coli* JM109/pBI18:GUS.

The plasmid pGKC18:GUS was further digested with restriction endonucleases Hind III and Sac I, and the resulting fragments were subjected to electrophoresis. After that, the Hind III-Sac I fragment was inserted at the Hind III/Sac I site in the plasmid pBI101-Hm2 to give novel plasmid pBI18:GUS. *E. coli* JM109 was then transformed with pBI18:GUS to give *E. coli* JM109/pBI18:GUS. The construction of this transformant is shown in FIG. 8.

(3) Introduction of Plasmid Into Agrobacterium

*E. coli* JM109/pBI18:GUS obtained in (2) and *E. coli* with helper plasmid pRK2013 were separately grown on LB media each containing 50 mg/l of kanamycin at 37° C. overnight, while Agrobacterium strain EHA101 (furnished by Prof. Atsuhiko Shinmyo in the Nara Institute of Science and Technology) was grown on LB medium containing 50 mg/l of kanamycin at 37° C. over two successive nights.

The bacterial cells were harvested by taking 1.5 ml of each of the cultures in an Eppendorf tube and then washed with LB medium. These bacterial cells were each suspended in 1 ml of LB medium, after which three kinds of bacteria were mixed together in 100 µl portions. The mixture was plated on LB agar medium and then incubated at 28° C. for the conjugation transfer of both plasmids to Agrobacterium. After 1 to 2 days, a part of the medium was scratched with a sterile loop and then spread over LB agar medium containing 50 mg/l kanamycin, 20 mg/l hygromycin B, and 25 mg/l chloramphenicol. After incubation at 28° C. for 2 days, a single colony was selected. The transformant thus obtained was designated EHA101/pBI18:GUS.

(4) Cultivation of Sterile *Arabidopsis thaliana*

Several dozens of seeds of *Arabidopsis thaliana* stain Wassilewskija (hereinafter referred to as strain WS) (furnished by Prof. Atsuhiko Shinmyo in the Nara Institute of Science and Technology) were placed in a 1.5 ml tube, to which 1 ml of 70% ethanol was added, and the seeds were left stand for 3 minutes. After that, the seeds were immersed in a solution for sterilization (5% sodium hypochlorite, 0.02% Triton X-100) for 3 minutes, washed five times with sterilized water, and then sowed on GM plate (4.3 g/l Murashige-Skoog inorganic salts, 10 g/l sucrose, 0.1 g/l of myoinositol, 5 g/l of Gellan gum; pH 5.7). This plate was left stand at 4° C. for 2 days for low temperature treatment, and cultivation was carried out in a plant incubator (model MLR-350HT, Sanyo Electric Co., Ltd.) at 22° C. under weak light for 7 days.

(5) Infection with Agrobacterium

The hypocotyls of several plants of the above strain WS cultivated for 7 days in (4) were arranged and then cut with a surgical knife to have a uniform length of about 1.0 cm. These cut pieces were placed side by side on CIM plate (containing 3.9 g/l Gamborg B5 medium salt mixture, 20 g/l glucose, 0.1 g/l myoinositol, 5 g/l Gellan gum, 0.5 µg/l 2,4-dichlorophenoxyacetic acid, 0.05 µg/l kinetin; pH 5.7) and then cultivated in the light period of 24 hours at a light intensity of 3000 lux for 2 days. The culture of transformant EHA101/pBI18:GUS obtained in (3), which had been incubated at 28° C. for 1 day, was 3-fold diluted with MS diluent (6.4 g/l Murashige-Skoog inorganic salts; pH 6.3), and the dilution was dispensed in 1 ml portions into several tubes. The hypocotyls in callus form cultivated on CIM medium for 2 days were immersed in these tubes for 10 minutes and then placed side by side on two layers of sterile filter papers to remove excess water. About twenty hypocotyls were transferred on each fresh CIM plate and then cocultivated for 2 days under the same conditions as described above.

(6) Sterilization

The cut pieces grown to an extent enough to observe the respective bacterial strains with the naked eye were placed in a solution for sterilization (prepared by adding claforan to MS diluent to yield a final concentration of 200 µg/ml) and then washed with gentle shaking for 60 minutes. After five repetitions of this procedure, these cut pieces were placed on a sterile filter paper to remove water, placed side by side on SIM plate (containing 3.9 g/l Gamborg B5 medium salt mixture, 20 g/l glucose, 0.1 g/l myoinositol, 5 g/l Gellan gum, 50 mg/l kanamycin, 20 mg/l hygromycin B, 0.2 g/l claforan, 0.5 g/l vancomycin, 5 mg/l 2iP, 0.15 mg/l IAA; pH 5.7), and then cultivated at a light intensity of 4000 lux for 2 days.

(7) Selection of Transformed Plants

The above cut pieces cultivated for 2 days in (6) were transferred to SIM plate and then cultivated at a light intensity of 4000 lux. After that, these cut pieces were transferred to fresh SIM plate every week. The transformed cut pieces were continuously grown to become dome-shaped swollen calli, whereas the non-transformants tuned brown in color. The calli of the transformants exhibited green color after about two weeks. After about one month, shoots were formed.

(8) Regeneration of Transformed Plants

Shoots were cut at their bases with a razor or a surgical knife so as not to include any callus, and slightly inserted into RIM plate (4.3 g/l MS salt, 10 g/l sucrose, 0.1 g/l myoinositol, 3.5 g/l Gellan gum, 0.02 mg/l of indolebutyric acid; pH 5.7) as if they were placed thereon. After about one month, the plant having several roots of about 1 to 2 cm in length was transplanted with a pincette in the soil prepared by mixing pearlite and vermiculite (TES Co.) at a ratio of 1:1 and soaking in an inorganic salts mixed medium. After about one month, a few hundred of seeds were obtained from each plant. These seeds are hereinafter referred to as T1 seeds.

(9) Selection of Antibiotic-resistant Strains

About one hundred T1 seeds were sterilized by the same method as described in (4) and then sowed in GM plate (containing 50 mg of kanamycin and 20 mg of hygromycin B). Kanamycin and hygromycin B-resistant strains were germinated at a ratio of approximately 3:1.

(10) Measurement of GUS Activity

Figure 9:
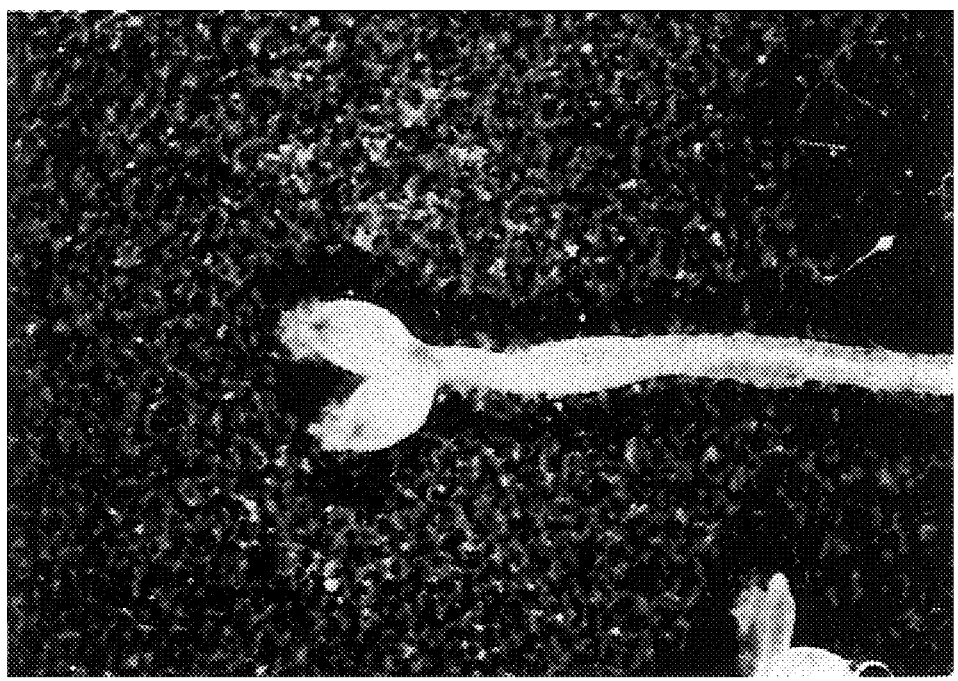
FIG. 9 is a photograph showing the GUS staining of transformed *Arabidopsis thaliana* after one-week growth in the dark.
Figure 10:
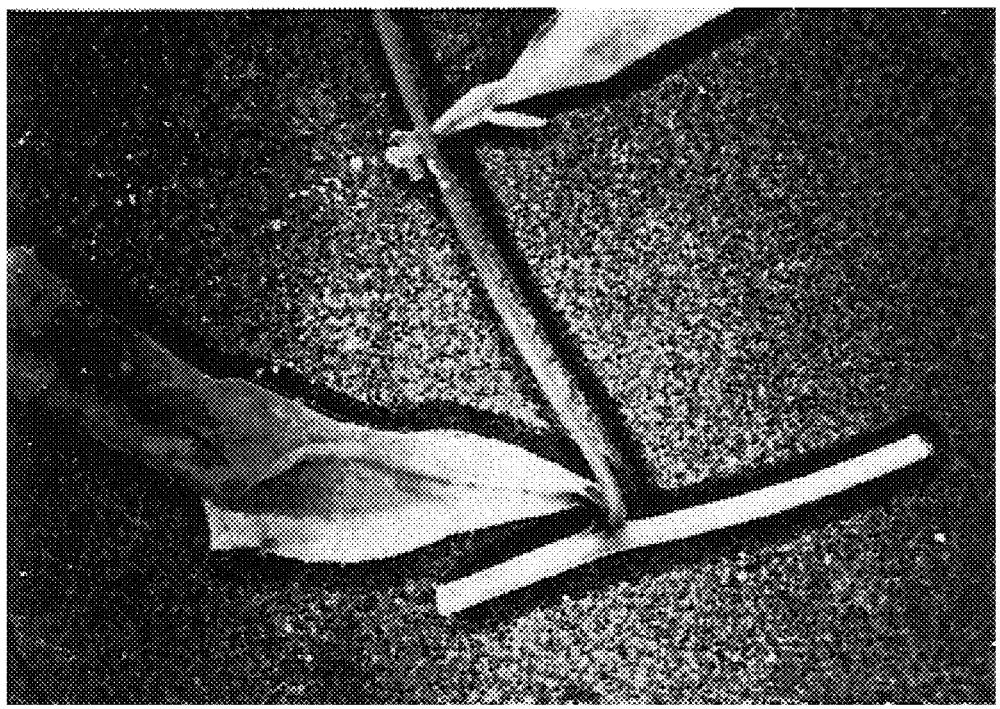
FIG. 10 is a photograph showing the GUS staining of transformed *Arabidopsis thaliana* after seven-week growth.
Figure 11:
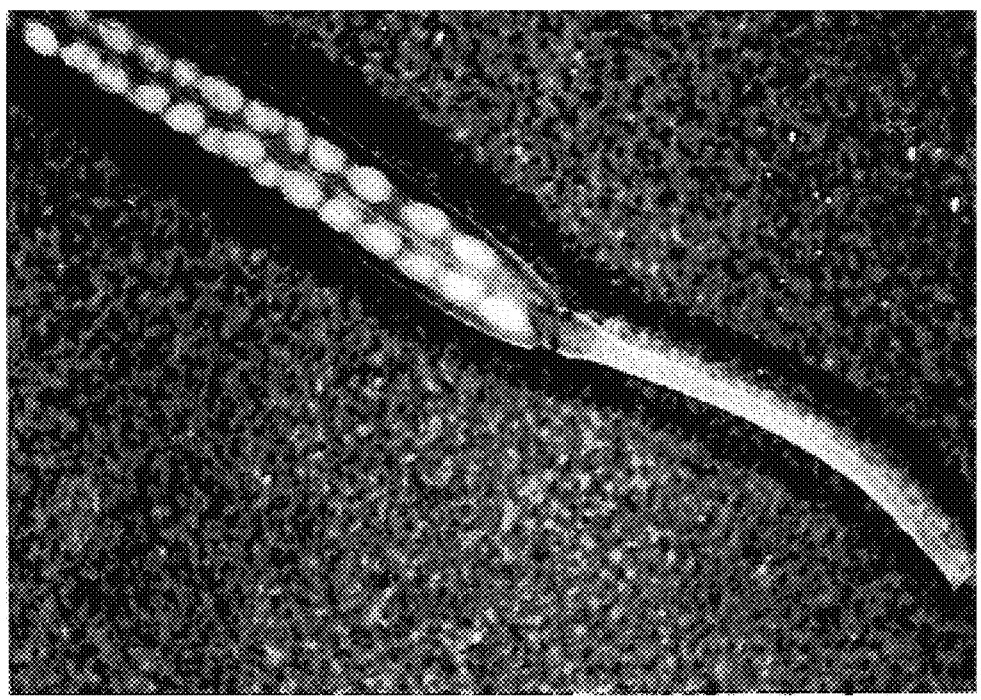
FIG. 11 is a photograph showing the GUS staining of transformed *Arabidopsis thaliana* after nine-week growth.

The transformed *Arabidopsis thaliana* as the homozygote obtained was cultivated. The tissues of this plant were cut with a surgical knife, and the cut pieces were immersed in several milliliters of fixing solution (0.03% formalin, 10 mM MES (pH 5.6), 0.3 M mannitol) at room temperature for 45 minutes. The cut pieces were washed several times with 50 mM phosphate buffer (pH 7.0). These cut pieces were immersed in the GUS staining solution (50 mM phosphate buffer, 0.5 M potassium ferricyanide, 0.5 M potassium ferrocyanide, 1 mM X-Gluc) and then treated under reduced pressure by suction with a vacuum pump, so that the solution was entirely absorbed into the inside of the sample, followed by overnight incubation at 37° C. For the removal of chlorophyll, the sample was immersed in 5% formalin for 10 minutes, and then immersed in 5% acetic acid for 10 minutes, in 50% ethanol for 10 minutes and in 100% ethanol for 10 hours. The blue-stained tissues were observed with a microscope, and the promoter function was confirmed even in *Arabidopsis thaliana*. In particular, expression was observed in the seedling as shown in FIG. 9. Expression was also observed in the leaves of the scape as shown in FIG. 10 and in the pod base on the 9th week as shown in FIG. 11. These results indicate that the DNA isolated in this Example functions as a promoter with tissue specificity, even in *Arabidopsis thaliana* which is a plant other than cotton plants.

Example 3

(1) Cloning of Upstream Region (GKC22) for Cotton Fiber Tissue-derived Gene KC22

The seedlings on the 18th day after the seeding of a cotton plant of the genus Gossypium were used to extract genomic DNA by an improved method of Murray and Thompson. The extracted genomic DNA was cloned by the inverse PCR method.

First, 1 µg of the genomic DNA was digested with restriction endonuclease Hind III, and the resulting fragments were self-ligated with T4 ligase. Then, 500 μg of the ligated DNA was used as a template for the amplification of the upstream region for KC22 (hereinafter referred to as GKC22) with a PCR reagent kit (LA-PCR kit, Takara Shuzo, Co., Ltd.). The reaction was effected with the first group of primers having the respective nucleotide sequences of SEQ ID NOs:12 and 13, and the steps of PCR at 94° C. for 15 seconds and at 65° C. for 12 minutes were repeated in 28 cycles. The PCR products were used for the subsequent PCR with the second group of primers having the respective nucleotide sequences of SEQ ID NOs:14 and 15 under the same conditions as described above. The PCR products were examined for amount and length by electrophoresis. The resulting DNA fragment was introduced into the vector pT7BlueT and then cloned by the transformation of E. coli JM109. The plasmid clone thus obtained was designated pGKC22. The nucleotide sequence of GKC22 was determined with a sequenase sequence kit (Amersham Corp.). The nucleotide sequence thus determined was completely the same as that of cDNA on the basis of the primer sequences, and it was, therefore, found to be a genomic region corresponding to the cDNA. The nucleotide sequence is shown in the Sequence Listing, SEQ ID NO:11.

(2) Fusion with β-glucuronidase (GUS) Gene

The plasmid pBI101-Hm2 containing β-glucuronidase (GUS) gene (furnished by Prof. Atsuhiko Shinmyo in the Nara Institute of Science and Technology) was digested with restriction endonucleases Hind III and Sac I, and the resulting fragments were subjected to agarose gel electrophoresis for the separation of the GUS gene from the plasmid. The GUS gene was inserted at the Hind III/Sac I site in the plasmid pUC19 to give plasmid pGUS.

The plasmid pGKC22 was digested with restriction endonucleases Hind III and Sty I, and further digested with restriction endonucleases Sty I and Dra I, and then inserted at the Hind III and Sma I site in the plasmid pGUS. The nucleotide sequence thus inserted was used for the determination of whether the fragment was correctly inserted or not. The plasmid with the correctly inserted fragment was designated pGKC22:GUS.

Figure 12:
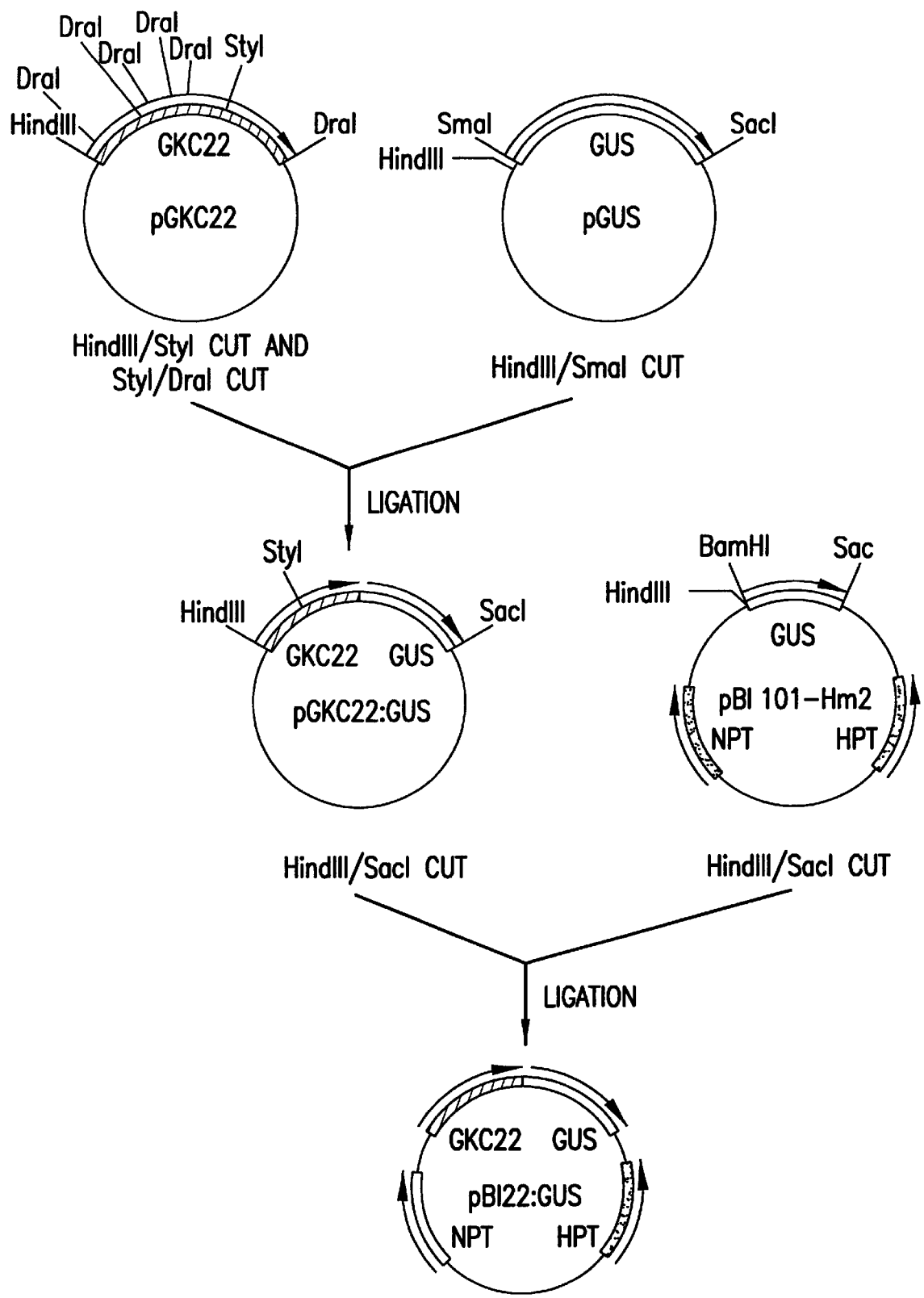
FIG. 12 is a diagram showing the construction of transformant *Escherichia coli* JM109/pBI22:GUS.

The plasmid pGKC22:GUS was further digested with restriction endonucleases Hind III and Sac I, and the resulting fragments were subjected to electrophoresis. After that, the Hind III-Sac I fragment was inserted at the Hind III/Sac I site in the plasmid pBI101-Hm2 to give novel plasmid pBI22:GUS. E. coli JM109 was then transformed with the pBI22:GUS to give E. coli JM109/pBI22:GUS. The construction of this transformant is shown in FIG. 12.

(3) Introduction of Plasmid Into Agrobacterium

E. coli JM109/pBI22:GUS obtained in (2) and E. coli with helper plasmid pRK2013 were separately grown on LB media each containing 50 mg/l of kanamycin at 37° C. overnight, while Agrobacterium strain EHA101 (furnished by Prof. Atsuhiko Shinmyo in the Nara Institute of Science and Technology) was grown on LB medium containing 50 mg/l of kanamycin at 37° C. over two successive nights.

The bacterial cells were harvested by taking 1.5 ml of each of the cultures in an Eppendorf tube and then washed with LB medium. These bacterial cells were each suspended in 1 ml of LB medium, after which three kinds of bacteria were mixed together in 100 μl portions. The mixture was plated on LB agar medium and then incubated at 28° C. for the conjugation transfer of both plasmids to Agrobacterium. After 1 to 2 days, a part of the medium was scratched with a sterile loop and then spread over LB agar medium containing 50 mg/l kanamycin, 20 mg/l hygromycin B, and 25 mg/l chloramphenicol. After incubation at 28° C. for 2 days, a single colony was selected. The transformant thus obtained was designated EHA101/pBI22:GUS.

(4) Cultivation of Sterile Arabidopsis thaliana

Several dozens of seeds of Arabidopsis thaliana stain Wassilewskija (hereinafter referred to as strain WS) (furnished by Prof. Atsuhiko Shinmyo in the Nara Institute of Science and Technology) were placed in a 1.5 ml tube, to which 1 ml of 70% ethanol was added, and the seeds were left stand for 3 minutes. After that, the seeds were immersed in a solution for sterilization (5% sodium hypochlorite, 0.02% Triton X-100) for 3 minutes, washed five times with sterilized water, and then sowed on GM plate (4.3 g/l Murashige-Skoog inorganic salts, 10 g/l sucrose, 0.1 g/l of myoinositol, 5 g/l of Gellan gum; pH 5.7). This plate was left stand at 4° C. for 2 days for low temperature treatment, and cultivation was carried out in a plant incubator (model MLR-350HT, Sanyo Electric Co., Ltd.) at 22° C. under weak light for 7 days.

(5) Infection with Agrobacterium

The hypocotyls of several plants of the above strain WS cultivated for 7 days in (4) were arranged and then cut with a surgical knife to have a uniform length of about 1.0 cm. These cut pieces were placed side by side on CIM plate (containing 3.9 g/l Gamborg B5 medium salt mixture, 20 g/l glucose, 0.1 g/l myoinositol, 5 g/l Gellan gum, 0.5 μg/l 2,4-dichlorophenoxyacetic acid, 0.05 μg/l kinetin; pH 5.7) and then cultivated in the light period of 24 hours at a light intensity of 3000 lux for 2 days. The culture of transformant EHA101/pBI03:GUS obtained in (3), which had been incubated at 28° C. for 1 day, was 3-fold diluted with MS diluent (6.4 g/l Murashige-Skoog inorganic salts; pH 6.3), and the dilution was dispensed in 1 ml portions into several tubes. The hypocotyls in callus form cultivated on CIM medium for 2 days were immersed in these tubes for 10 minutes and then placed side by side on two layers of sterile filter papers to remove excess water. About twenty hypocotyls were transferred on each fresh CIM plate and then cocultivated for 2 days under the same conditions as described above.

(6) Sterilization

The cut pieces grown to an extent enough to observe the respective bacterial strains with the naked eye were placed in a solution for sterilization (prepared by adding claforan to MS diluent to yield a final concentration of 200 μg/ml) and then washed with gentle shaking for 60 minutes. After five repetitions of this procedure, these cut pieces were placed on a sterile filter paper to remove water, placed side by side on SIM plate (containing 3.9 g/l Gamborg B5 medium salt mixture, 20 g/l glucose, 0.1 g/l myoinositol 5 g/l Gellan gum, 50 mg/l kanamycin, 20 mg/l hygromycin B, 0.2 g/l claforan, 0.5 g/l vancomycin, 5 mg/l 2iP, 0.15 mg/l IAA; pH 5.7), and then cultivated at a light intensity of 4000 lux for 2 days.

(7) Selection of Transformed Plants

The above cut pieces cultivated for 2 days in (6) were transferred to SIM plate and then cultivated at a light intensity of 4000 lux. After that, these cut pieces were transferred to fresh SIM plate every week. The transformed cut pieces were continuously grown to become dome-shaped swollen calli, whereas the non-transformants turned brown in color. The calli of the transformants exhibited green color after about two weeks. After about one month, shoots were formed.

(8) Regeneration of Transformed Plants

Shoots were cut at their bases with a razor or a surgical knife so as not to include any callus, and slightly inserted into RIM plate (4.3 g/l MS salt, 10 g/l sucrose, 0.1 g/l myoinositol, 3.5 g/l Gellan gum, 0.02 mg/l of indolebutyric acid; pH 5.7) as if they were placed thereon. After about one month, the plant having several roots of about 1 to 2 cm in length was transplanted with a pincette in the soil prepared by mixing pearlite and vermiculite (TES Co.) at a ratio of 1:1 and soaking in an inorganic salts mixed medium. After about one month, a few hundred of seeds were obtained from each plant. These seeds are hereinafter referred to as T1 seeds.

(9) Selection of Antibiotic-resistant Strains

About one hundred T1 seeds were sterilized by the same method as described in (4) and then sowed in GM plate (containing 50 mg of kanamycin and 20 mg of hygromycin B). Kanamycin and hygromycin B-resistant strains were germinated at a ratio of approximately 3:1.

(10) Measurement of GUS Activity

Figure 13:
FIG. 13 is a photograph showing the GUS staining of transformed *Arabidopsis thaliana* after one-week growth in the dark.
Figure 14:
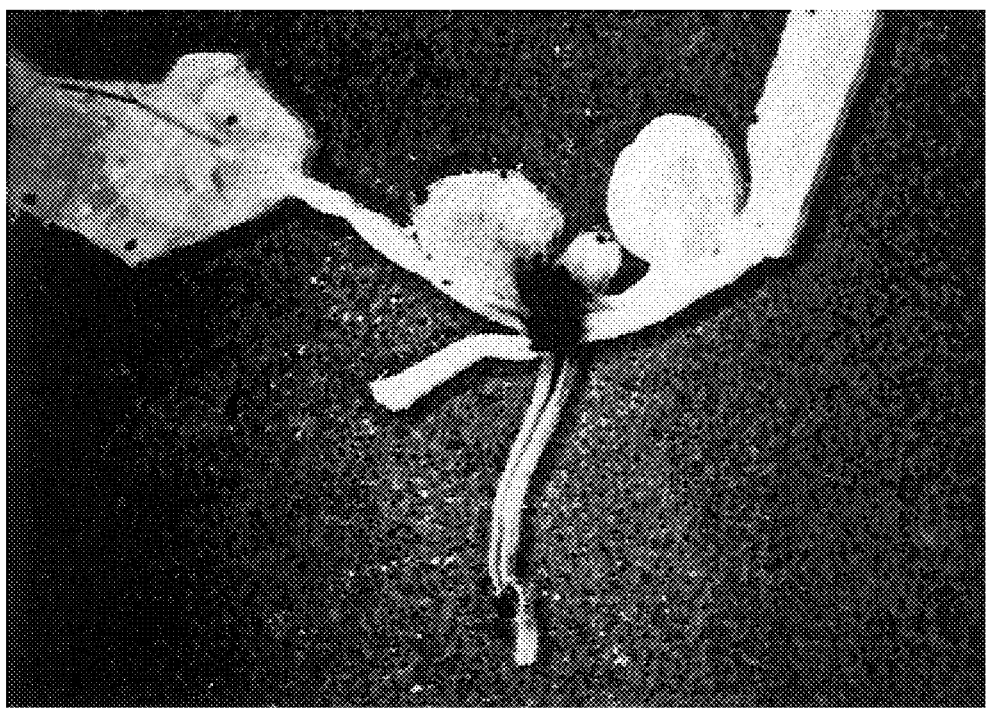
FIG. 14 is a photograph showing the GUS staining of the transformed *Arabidopsis thaliana* after three-week growth.
Figure 15:
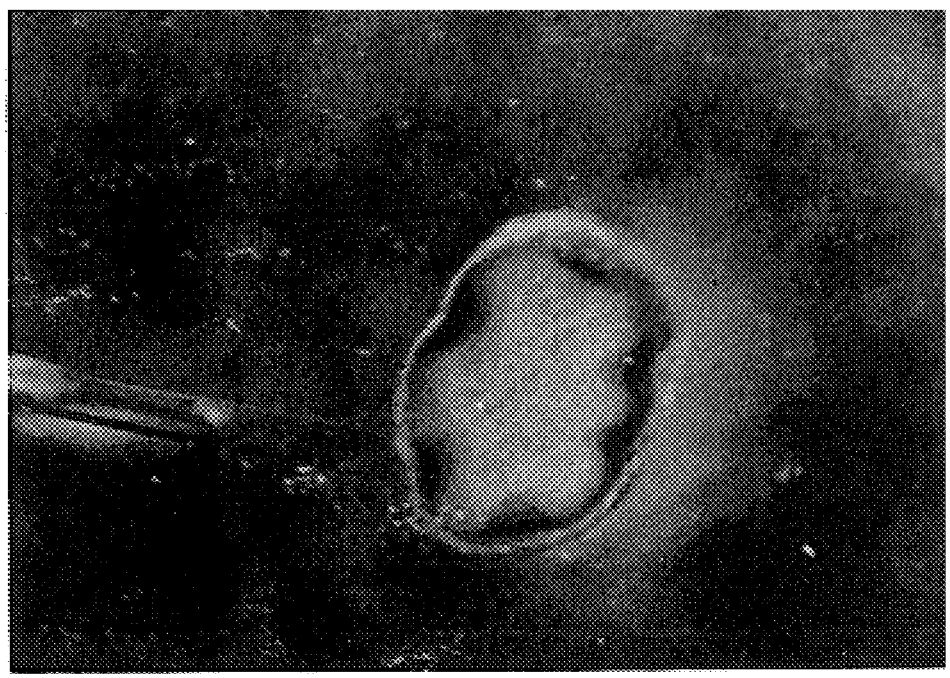
FIG. 15 is a photograph showing the GUS staining of a section of the petiole of the transformed *Arabidopsis thaliana* after three-week growth.
Figure 16:
FIG. 16 is a photograph showing the GUS staining of flowers of the transformed *Arabidopsis thaliana* after seven-week growth.
Figure 17:
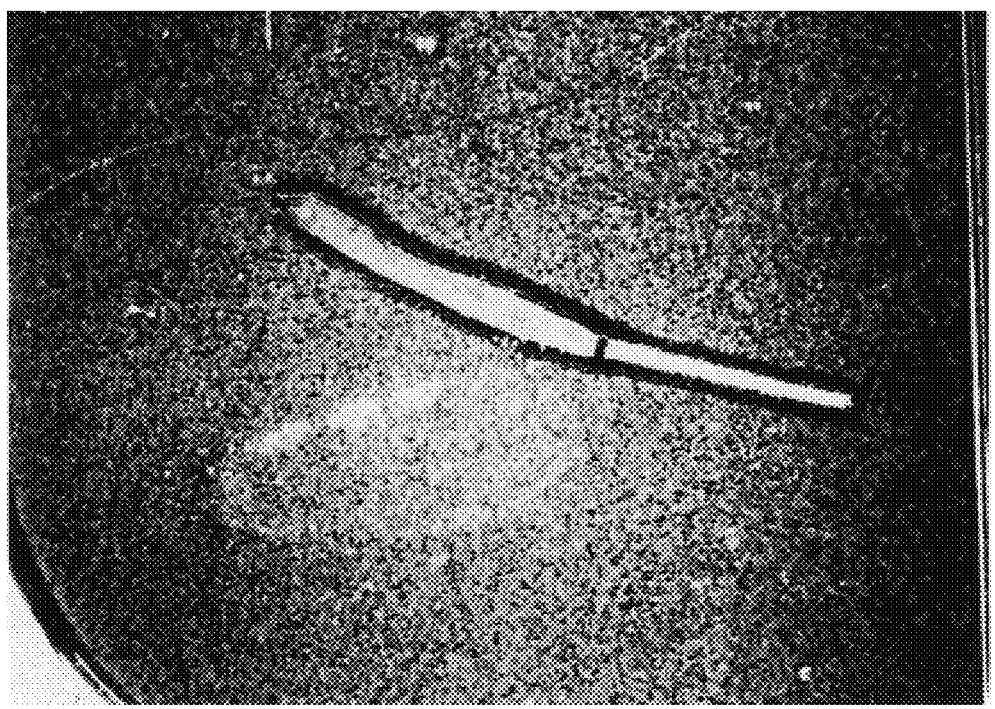
FIG. 17 is a photograph showing the GUS staining of a pod base of the transformed *Arabidopsis thaliana* after nine-week growth.

The transformed *Arabidopsis thaliana* as the homozygote obtained was cultivated. The tissues of this plant were cut with a surgical knife, and the cut pieces were immersed in several milliliters of fixing solution (0.03% formalin, 10 mM MES (pH 5.6), 0.3 M mannitol) at room temperature for 45 minutes. The cut pieces were washed several times with 50 mM phosphate buffer (pH 7.0). These cut pieces were immersed in the GUS staining solution (50 mM phosphate buffer, 0.5 M potassium ferricyanide, 0.5 M potassium ferrocyanide, 1 mM X-Gluc) and then treated under reduced pressure by suction with a vacuum pump, so that the solution was entirely absorbed into the inside of the sample, followed by overnight incubation at 37° C. For the removal of chlorophyll, the sample was immersed in 5% formalin for 10 minutes, and then immersed in 5% acetic acid for 10 minutes, in 50% ethanol for 10 minutes and in 100% ethanol for 10 hours. The blue-stained tissues were observed with a microscope, and the promoter function was confirmed even in *Arabidopsis thaliana*. In particular, strong expression was observed in the vascular bundle system of the seedlings as shown in FIGS. 13, 14 and 15. Expression was also observed in the pistil and stamen apices of the flower as shown in FIG. 16, and in the pod base and apex on the 9th week as shown in FIG. 17. These results indicate that the DNA isolated in this Example functions as a promoter with tissue specificity, even in *Arabidopsis thaliana* which is a plant other than cotton plants.

Example 4

(1) Cloning of Upstream Region (Gh10) for Cotton Fiber Tissue-derived Gene Gh3

The leaves of the seedlings on the 100th day after the seeding of a cotton plant of the genus Gossypium (Coker 312) were used to extract genomic DNA by an improved method of Murray and Thompson. The extracted genomic DNA was cloned by the inverse PCR method.

First, 1 μg of the genomic DNA was digested with restriction endonuclease EcoR I, and the resulting fragments were self-ligated with T4 ligase. Then, 500 μg of the ligated DNA was used as a template for the amplification of the upstream region for Gh3 (hereinafter referred to as Gh10) with TaqDNA polymerase. The reaction was effected with the first group of primers having the respective nucleotide sequences of SEQ ID NOs:17 and 18, and the steps of PCR at 98° C. for 30 seconds and at 68° C. for 6 minutes were repeated in 35 cycles. The PCR products were used for the subsequent PCR with the second group of primers having the respective nucleotide sequences of SEQ ID NOs:19 and 20 under the same conditions as described above. The PCR products were examined for amount and length by electrophoresis. The resulting DNA fragment was introduced into the vector pGEM-T (Promega Corp.) and then cloned by the transformation of *E. coli* JM109. The plasmid clone thus obtained was designated pGh10. The nucleotide sequence of pGh10 was determined with a sequenase sequence kit (Amersham Corp.). The nucleotide sequence thus determined was completely the same as that of cDNA on the basis of the primer sequences, and it was, therefore, found to be a genomic region corresponding to the cDNA The nucleotide sequence is shown in the Sequence Listing, SEQ ID NO:16.

(2) Fusion with β-glucuronidase (GUS) Gene

The 3'-terminal primer (5'-GCAATAGAAGCCATGGGAGAGAG-3') (SEQ ID NO:21) with a restriction endonuclease Nco I site was synthesized. This primer and T7 primer were used for the amplification of a 1069 bp fragment. This fragment was sub-cloned into pGEM-T vector by the use of the restriction endonuclease site. The sub-cloned vector was digested with restriction endonucleases Pst I and Nco I, and the resulting fragment was ligated with GUS reporter gene and 35S terminator. The correctly ligated plasmid was designated pGh10:GUS.

Figure 18:
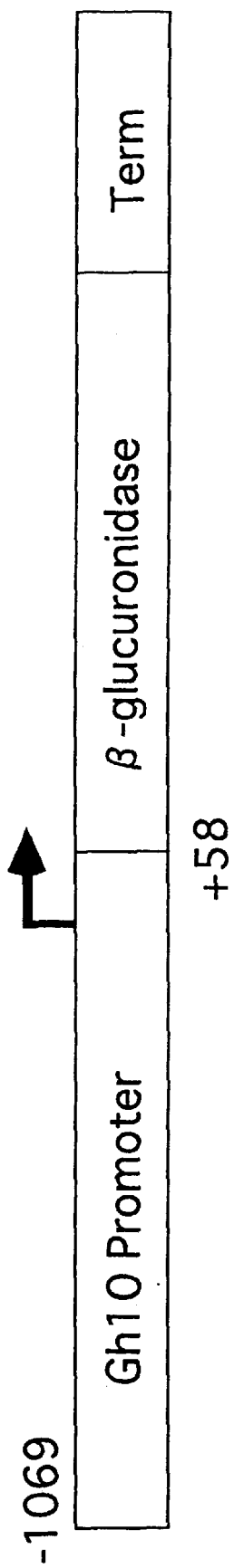
FIG. 18 is a diagram showing the pGh10:GUS chimera gene construct. The GUS (β-glucuronidase) reporter gene was linked with the Gh10 promoter. This gene construct was used to produce transgenic cotton plants by Agrobacterium infection.

The plasmid pGh10:GUS was digested with restriction endonuclease Pst I, and the resulting fragments were subjected to electrophoresis. After that, the fragment was inserted at the Pst I site in the binary vector pCGN1578 to give novel plasmid pCGN-Gh10:GUS as shown in FIG. 18. *E. coli* JM109 was then transformed with the pCGN-Gh10:GUS to give *E. coli* JM109/pCGN-Gh10:GUS.

(3) Introduction of Plasmid into Agrobacterium

*E. coli* JM109/pCGN-Gh10:GUS obtained in (2) and *E. coli* with helper plasmid pRK2013 were separately grown on LB media each containing 50 mg/l of kanamycin at 37° C. overnight, while Agrobacterium strain EHA101 was grown on LB medium containing 50 mg/l of kanamycin at 37° C. over two successive nights.

The bacterial cells were harvested by taking 1.5 ml of each of the cultures in an Eppendorf tube and then washed with LB medium. These bacterial cells were each suspended in 1 ml of LB medium, after which three kinds of bacteria were mixed together in 100 μl portions. The mixture was plated on LB agar medium and then incubated at 28° C. for the conjugation transfer of both plasmids to Agrobacterium. After 1 to 2 days, a part of the medium was scratched with a sterile loop and then spread over LB agar medium containing 50 mg/l kanamycin, 20 mg/l hygromycin B, and 25 mg/l chloramphenicol. After incubation at 28° C. for 2 days, a single colony was selected. The transformant thus obtained was designated EHA101/pCGN-Gh10:GUS.

(4) Preparation of Transformed Cotton Plants

The Agrobacterium EHA101/pCGN:Gh10:GUS was used for the transformant of a cotton plant (Coker 312). The method reported by N. Trolinder et al. (Theor. Appl. Genet. (1992) 83:645–649) was employed for the transformation. The seeds of the cotton plant (Coker 312) were sterilized with 3% aqueous sodium hypochlorite solution for 20 minutes and then washed three times with sterilized water containing cefotaxime. These seeds were germinated on Stewart medium for 6 days. The hypocotyls were cut into pieces of 5 mm in length and then infected with about 10 μl of overnight culture of Agrobacterium. The infected hypocotyls were placed on 0.8% agarose medium and then left in the dark at room temperature for 3 days. These hypocotyls were pre-cultured on MS medium containing B5 vitamin, 30 g/l glucose, 0.1 mg/ml 2,4-D, 0.5 mg/l kinetin, 1.6 mg/ml Gelrite (Kelco), and 750 μg/ml magnesium chloride at 30° C. for 3 days. As the antibiotics, 50 μg/l kanamycin and 500 μg/l cefotaxime were used. After that, subculturing was carried out every four weeks.

The initiation and maintenance of cell suspension culture were carried out as follows: When the calli of the cotton plant (Coker 312) came to have a diameter of about 1 cm, they were transferred to the suspension culture. The medium had the same composition as that of the callus initiation medium, but it did not contain any hormone or gelling agent. For 10 ml of suspension culture, about 100 mg of calli were used. The culture was incubated at 120 rpm under illumination at 30° C. The subculturing was carried out every about one month.

The cell suspension culture was plated, and the development of embryos was effected on semi-solid medium.

Figure 19:
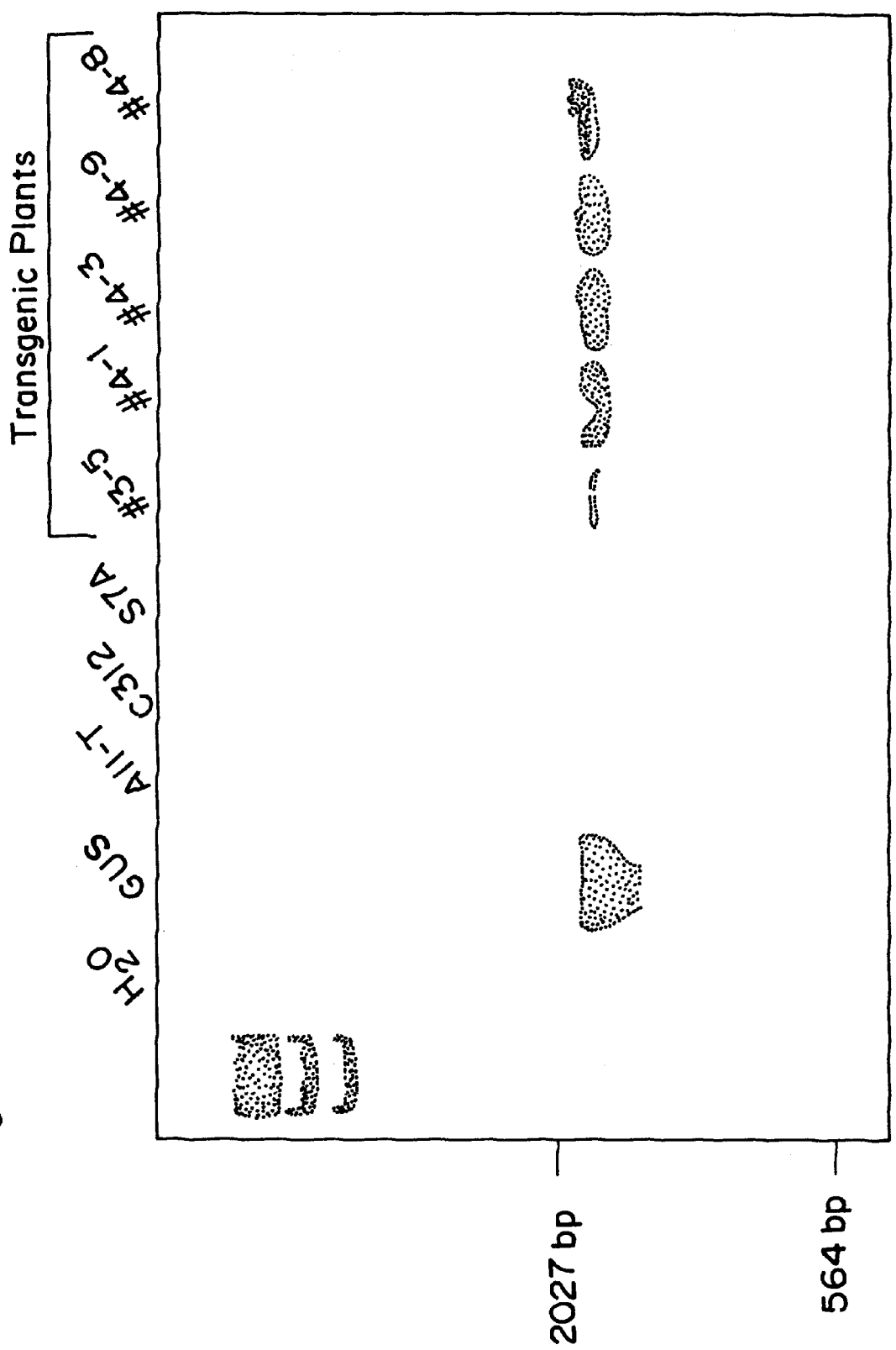
FIG. 19 is a view showing the result of a PCR analysis of transformed cotton genomic DNA to confirm the introduction of a desired gene.

For the germination of embryos and regeneration of plants, matured embryos grown up to 1 cm or longer were used, and they were cultivated in a 25 mm×150 mm culture tube. The culture tube was filled with vermiculite that had been soaked with Stewart and Hsu medium containing 0.1 mg/l IAA. The embryos were cultivated at 28° C. under illumination of $90 \mu Em^{-2}g^{-1}$. Both in the germination and in the shoot formation, fresh medium was added to the vermiculite. Finally, plural transformed cotton plants were obtained. In particular, transformed cotton plant lines #3-5, #4-1, #4-3, #4-9, and #4-8 were determined for whether the gene was introduced or not by the PCR analysis of their genomic DNA As a result, a DNA fragment was obtained clearly showing the introduction of the gene as shown in FIG. 19.

(5) Measurement of GUS Activity

Figure 20:
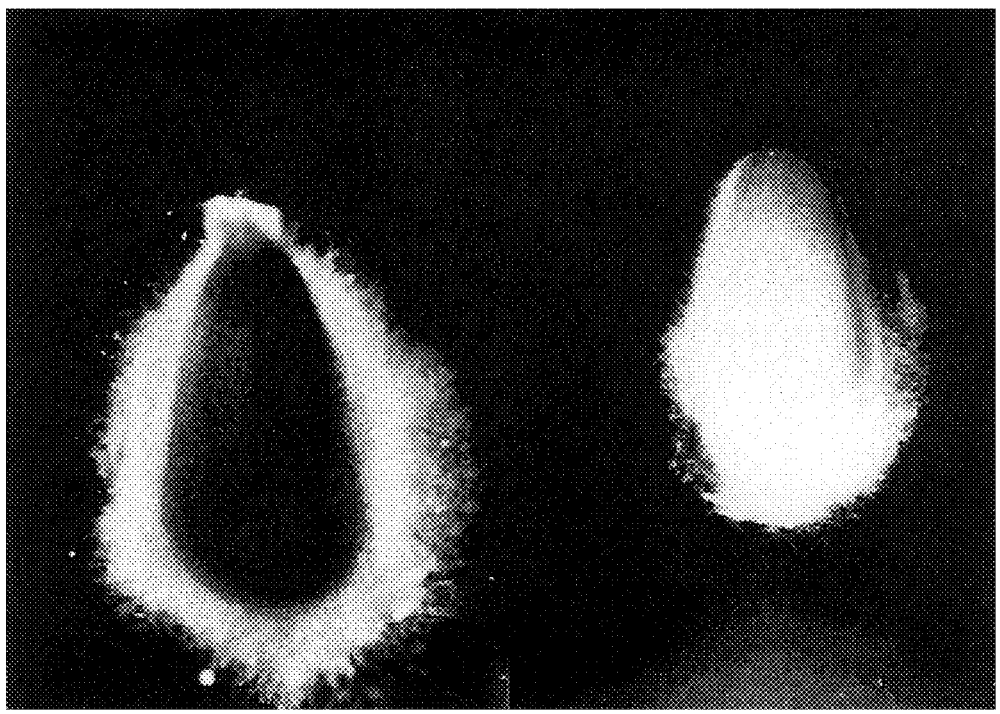
FIG. 20 is a photograph showing the GUS staining of cotton ovules after two days from the flowering.
Figure 21:
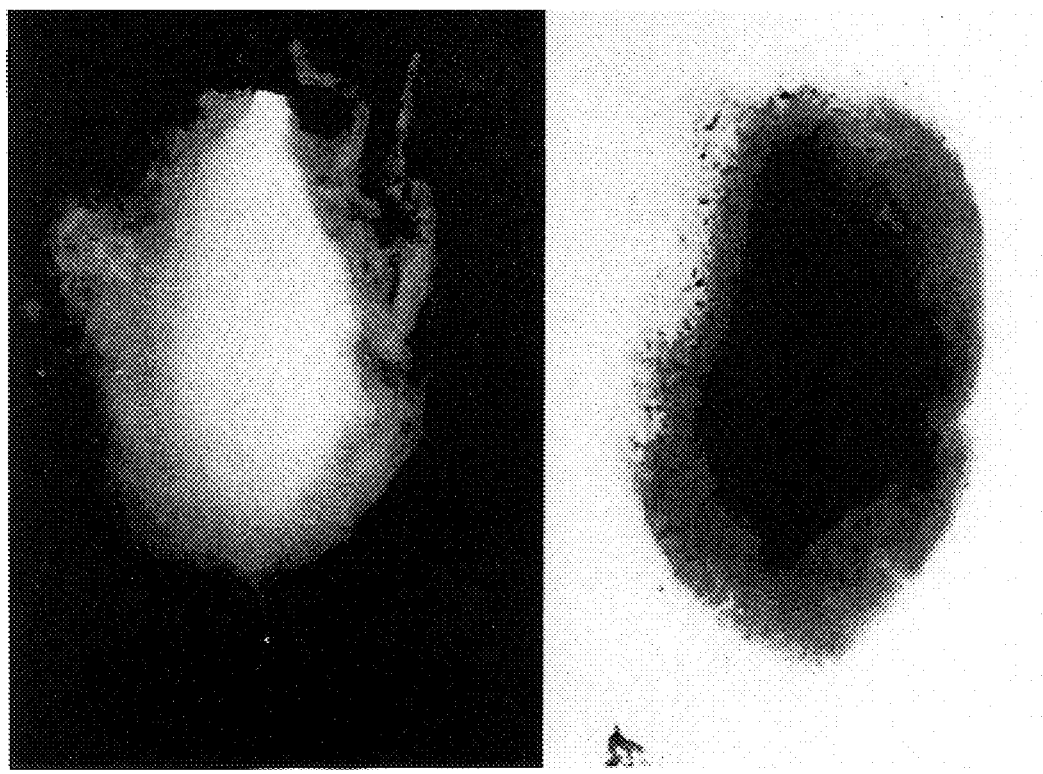
FIG. 21 is a photograph showing the GUS staining of cotton ovules after twelve days from the flowering.
Figure 22:
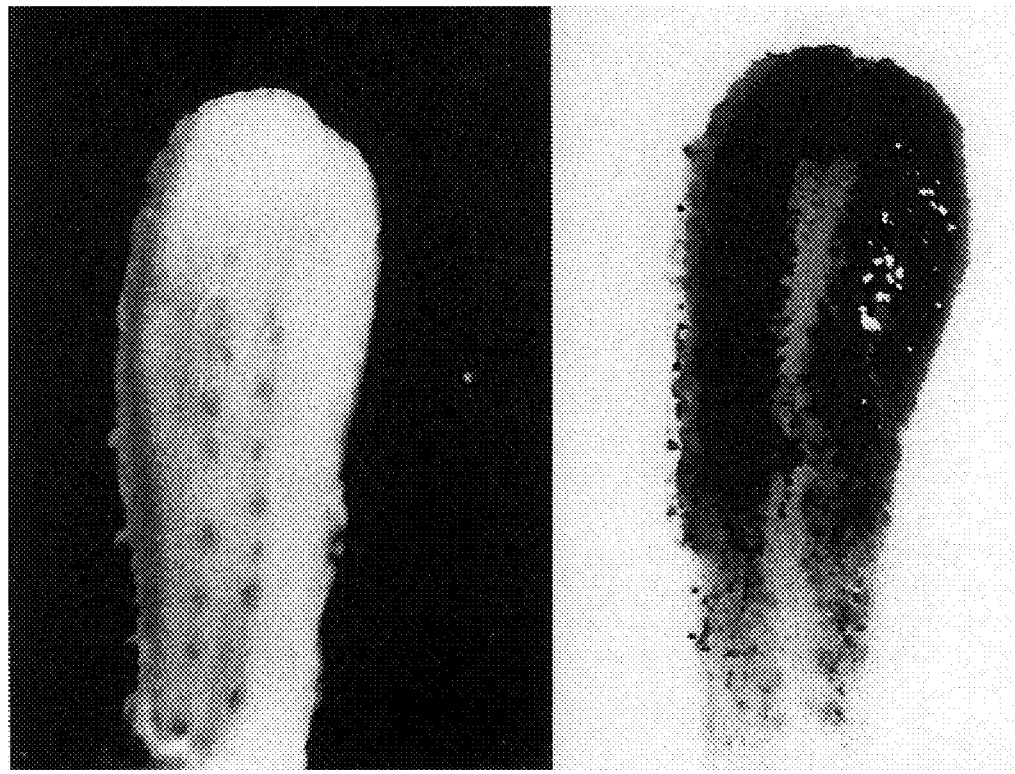
FIG. 22 is a photograph showing the GUS staining of cotton styles.
Figure 23:
FIG. 23 is a photograph showing the GUS staining of cotton anthers.

The transformed cotton plants obtained were cultivated. The tissues of these plants were cut with a surgical knife, and the cut pieces were immersed in several milliliters of fixing solution (0.03% formalin, 10 mM MES (pH 5.6), 0.3 M mannitol) at room temperature for 45 minutes. The cut pieces were washed several times with 50 mM phosphate buffer (pH 7.0). These cut pieces were immersed in the GUS staining solution (50 mM phosphate buffer, 0.5 M potassium ferricyanide, 0.5 M potassium ferrocyanide, 1 mM X-Gluc) and then treated under reduced pressure by suction with a vacuum pump, so that the solution was entirely absorbed into the inside of the sample, followed by overnight incubation at 37° C. For the removal of chlorophyll, the sample was immersed in 5% formalin for 10 minutes, and then immersed in 5% acetic acid for 10 minutes, in 50% ethanol for 10 minutes and in 100% ethanol for 10 hours. The blue-stained tissues were observed with a microscope, and the promoter function was confirmed in the transformed cotton plants. The fibers on the 2nd day after flowering were stained, whereas no staining was observed in the wild-type cotton plant on that day, as shown by the left and right pictures, respectively, in FIG. 20. The fibers on the 12th day after flowering were also stained, whereas no staining was observed in the wild-type cotton plant on that day, as shown by the right and left pictures, respectively, in FIG. 21. The style was also stained, whereas no staining was observed in the wild-type cotton plant, as shown by the right and left pictures, respectively, in FIG. 22. The anther was also stained, whereas no staining was observed in the wild-type cotton plant, as shown by the left and right pictures, respectively, in FIG. 23.

Figure 24:
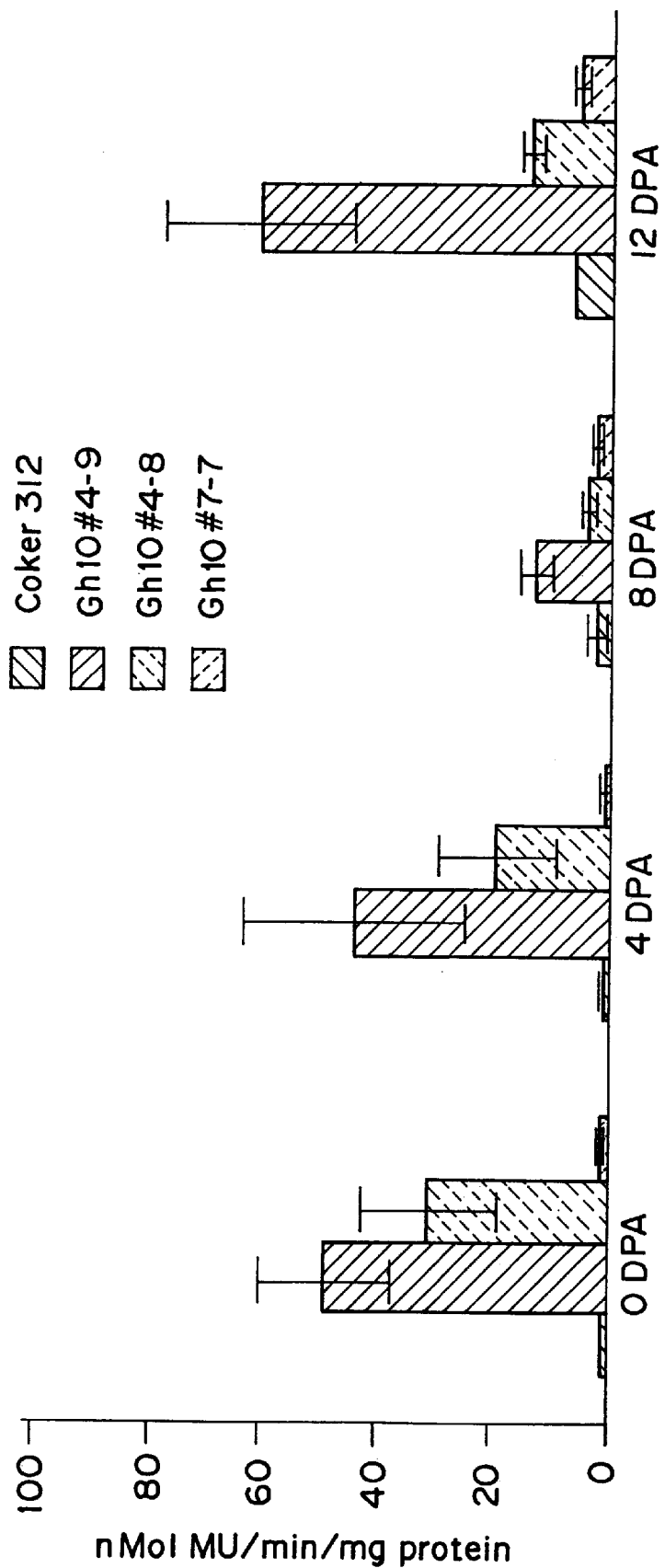
FIG. 24 is a graph showing the result of a fluorometric assay of Gh10/GUS expression in developing ovules. In this figure, "DPA" is an abbreviation for "days post-anthesis," and for example, "4 DPA" represents the 4th day after flowering.
Figure 25:
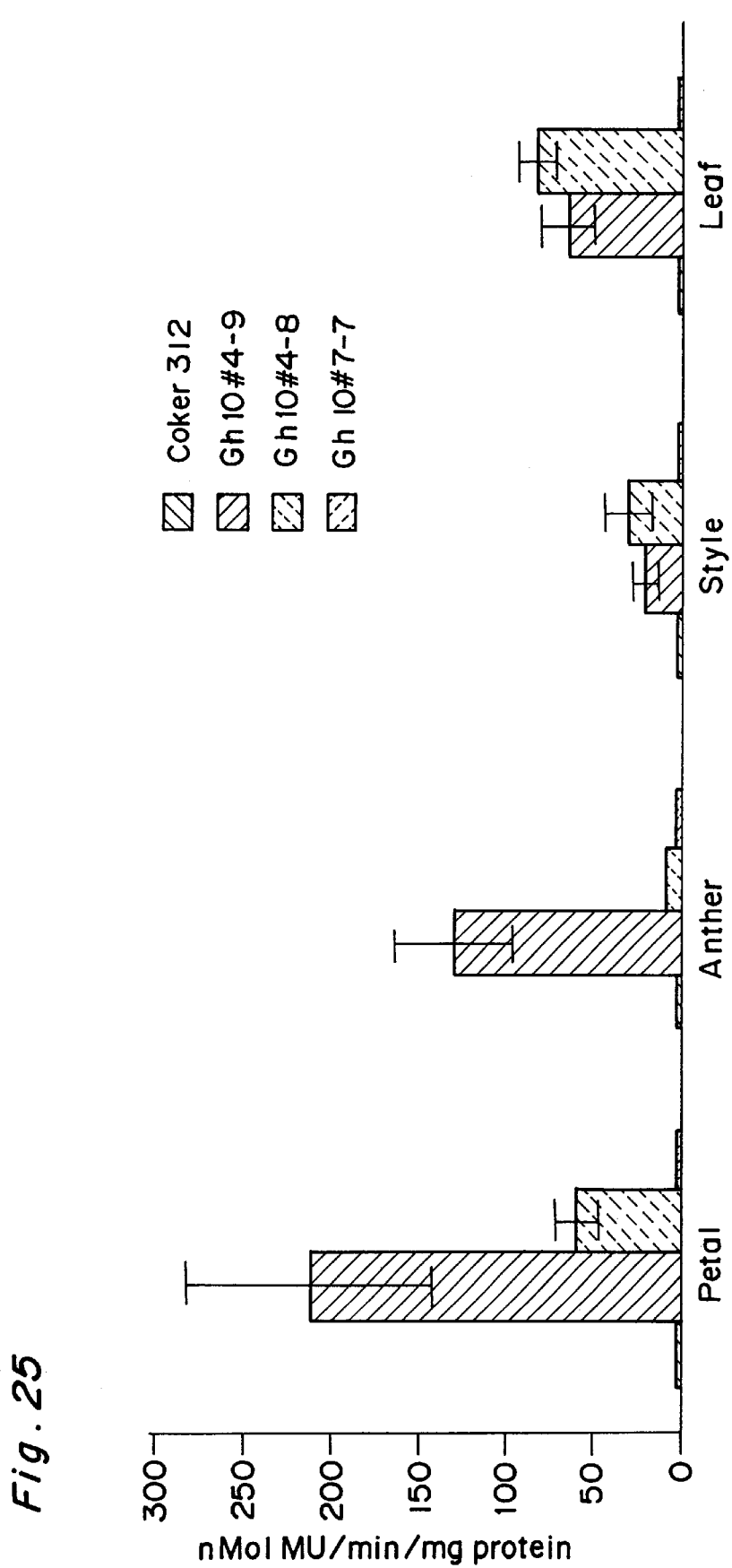
FIG. 25 is a graph showing the result of a fluorometric assay of Gh10/GUS expression in different tissues.

The measurement of GUS activity confirmed the expression of strong GUS activity in the developing ovules of the transformed cotton plant lines #4-8 and #4-9 as shown in FIG. 24. The measurement of GUS activity in different tissues further confirmed the expression of GUS activity in the styles, anthers, leaves, and petals as shown in FIG. 25.

From these results, it is clear that Gh10 promoter has promoter function in the fibers, petals, anthers, styles, and leaves of cotton plants.

What is claimed is:

1. An isolated and functional cotton plant promoter comprising DNA having the nucleotide sequence of SEQ ID NO:1, 6, 11 or 16.

2. An isolated and functional cotton plant promoter comprising DNA having the nucleotide sequence of SEQ ID NO:1.

3. An isolated and functional cotton plant promoter comprising DNA having the nucleotide sequence of SEQ ID NO:6.

4. An isolated and functional cotton plant promoter comprising DNA having the nucleotide sequence of SEQ ID NO:11.

5. An isolated and functional cotton plant promoter comprising DNA having the nucleotide sequence of SEQ ID NO:16.

6. A cotton plant expression vector prepared by introducing the cotton plant promoter of claim 1 into a vector functional in a cotton plant host cell.

7. A cotton plant expression vector prepared by introducing the cotton plant promoter of claim 2 into a vector functional in a cotton plant host cell.

8. A cotton plant expression vector prepared by introducing the cotton plant promoter of claim 3 into a vector functional in a cotton plant host cell.

9. A cotton plant expression vector prepared by introducing the cotton plant promoter of claim 4 into a vector functional in a cotton plant host cell.

10. A cotton plant expression vector prepared by introducing the cotton plant promoter of claim 5 into a vector functional in a cotton plant host cell.

11. A transformed cotton plant cell prepared by transforming a host cotton plant cell with the cotton plant expression vector of claim 6.

12. A transformed cotton plant cell prepared by transforming a host cotton plant cell with the cotton plant expression vector of claim 7.

13. A transformed cotton plant cell prepared by transforming a host cotton plant cell with the cotton plant expression vector of claim 8.

14. A transformed cotton plant cell prepared by transforming a host cotton plant cell with the cotton plant expression vector of claim 9.

15. A transformed cotton plant cell prepared by transforming a host cotton plant cell with the cotton plant expression vector of claim 10.

16. A transformed cotton plant regenerated from the transformed cotton plant cell of claim 11.

17. A transformed cotton plant regenerated from the transformed cotton plant cell of claim 12.

18. A transformed cotton plant regenerated from the transformed cotton plant cell of claim 13.

19. A transformed cotton plant regenerated from the transformed cotton plant cell of claim 14.

20. A transformed cotton plant regenerated from the transformed cotton plant cell of claim 15.

21. A cotton plant seed obtained from the transformed cotton plant of claim 16.

22. A cotton plant seed obtained from the transformed cotton plant of claim 17.

23. A cotton plant seed obtained from the transformed cotton plant of claim 18.

24. A cotton plant seed obtained from the transformed cotton plant of claim 19.

25. A cotton plant seed obtained from the transformed cotton plant of claim 20.

26. A process for producing a cotton plant, comprising the steps:
   transforming a host cotton cell with an expression vector comprising a cotton plant promoter comprising DNA having the nucleotide sequence of SEQ ID NO:1, 6, 11 or 16, resulting in a transformed cotton cell;
   regenerating a transformed cotton plant from the transformed cotton cell;
   obtaining a cotton seed from the transformed cotton plant; and
   producing a cotton plant transformed with said cotton plant promoter from the cotton seed.

27. A process for producing a cotton plant, comprising the steps:
   transforming a host cotton cell with an expression vector comprising a cotton plant promoter comprising DNA having the nucleotide sequence of SEQ ID NO:1, resulting in a transformed cotton cell;
   regenerating a transformed cotton plant from the transformed cotton cell;
   obtaining a cotton seed from the transformed cotton plant; and
   producing a cotton plant transformed with said cotton plant promoter from the cotton seed.

28. A process for producing a cotton plant, comprising the steps:
   transforming a host cotton cell with an expression vector comprising a cotton plant promoter comprising DNA having the nucleotide sequence of SEQ ID NO: 6, resulting in a transformed cotton cell;
   regenerating a transformed cotton plant from the transformed cotton cell;
   obtaining a cotton seed from the transformed cotton plant; and
   producing a cotton plant transformed with said cotton plant promoter from the cotton seed.

29. A process for producing a cotton plant, comprising the steps:
   transforming a host cotton cell with an expression vector comprising a cotton plant promoter comprising DNA having the nucleotide sequence of SEQ ID NO: 11, resulting in a transformed cotton cell;
   regenerating a transformed cotton plant from the transformed cotton cell;
   obtaining a cotton seed from the transformed cotton plant; and
   producing a cotton plant transformed with said cotton plant promoter from the cotton seed.

30. A process for producing a cotton plant, comprising the steps:
   transforming a host cotton cell with an expression vector comprising a cotton plant promoter comprising DNA having the nucleotide sequence of SEQ ID NO: 16, resulting in a transformed cotton cell;
   regenerating a transformed cotton plant from the transformed cotton cell;
   obtaining a cotton seed from the transformed cotton plant; and
   producing a cotton plant transformed with said cotton plant promoter from the cotton seed.

* * * * *